United States Patent [19]
Hiebert et al.

[11] Patent Number: 5,428,021
[45] Date of Patent: Jun. 27, 1995

[54] HUMAN LEUKOCYTE ELASTASE (HLE) INHIBITORS, AND RELATED PHARMACEUTICAL COMPOSITIONS AND METHODS OF USE

[75] Inventors: Charles K. Hiebert, Mountain View; Alan Laibelman, Menlo Park; Kenneth J. Ryan, Sunnyvale, all of Calif.

[73] Assignee: SRI International, Menlo Park, Calif.

[21] Appl. No.: 188,579

[22] Filed: Jan. 27, 1994

[51] Int. Cl.$^6$ .............. A61K 38/05; A61K 38/06; A61K 31/535; C07D 265/24
[52] U.S. Cl. ............................ 514/18; 514/19; 514/230.5; 544/92; 530/331
[58] Field of Search .............. 514/18, 19, 230.5; 544/92; 530/331

[56] References Cited

U.S. PATENT DOCUMENTS 4,980,287 12/1990 Kokubo et al. ................. 435/184

FOREIGN PATENT DOCUMENTS 0466944 1/1992 European Pat. Off. .

OTHER PUBLICATIONS

Krantz et al. (1990) *J. Med. Chem.* 33:464–479.
H. Carp et al., Potential mechanism of emphysema: $\alpha_1$-Proteinase inhibitor recovered from lungs of cigarette smokers contains oxidized methionine and has decreased elastase inhibitory capacity, *Proc. Natl. Acad. Sci.* 770:2041–2045 (1982).
L. J. Copp, et al., Kinetics and mechanism of human leukocyte elastase inactivation by ynenol lactones *Biochemistry* 26:169–178 (1987).
P. D. Edwards, Design, synthesis, and kinetic evaluation of a unique class of elastase inhibitors, the peptidyl $\alpha$-Ketobenzoxazoles, and the X-ray crystal structure of the covalent complex between porcine pancreatic elastase and Ac-Ala-Pro-Val-2-Benzoxazole, *J. Am. Chem. Soc.* 114:1854–1863 (1992).
L. Eskerot et al., Interactions of granulocyte proteases with inhibitors in rheumatoid arthritis, *Adv. Exp. Med. Biol.* 167:335–344 (1984).
P. E. Finke, et al., Inhibition of human leukocyte elastase. 4. Selection of a substituted cephalosporin (L-658,758) as a topical aerosol, *J. Med. Chem.* 35:3731–3744 (1992).

(List continued on next page.)

*Primary Examiner*—Mukund J. Shah
*Assistant Examiner*—Matthew V. Grumbling
*Attorney, Agent, or Firm*—Dianne E. Reed

[57] ABSTRACT

Novel therapeutic agents useful as inhibitors of HLE are provided. The compounds have the structural formula (I)

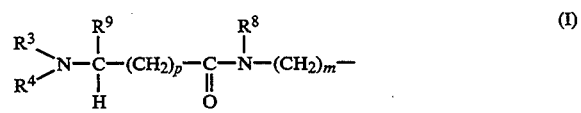

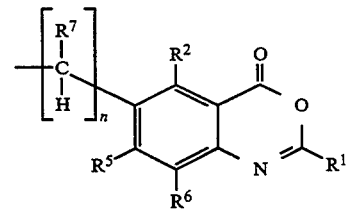

wherein $R^1$ through $R^9$, m, n and p are as defined herein. Methods of using the compounds of formula (I) to inhibit serine proteases and to treat physiological conditions and disease states associated with elevated HLE levels are also provided, as are pharmaceutical compositions containing the compounds.

16 Claims, No Drawings

OTHER PUBLICATIONS

J. W. Harper, et al., Reaction of serine proteases with substituted 3-Alkoxy-4-chloroisocoumarins and 3-Alkoxy-7-amino-4-chloroisocoumarins: New reactive mechanism-based inhibitors, *Biochemistry* 24:7200–7213 (1985).

J. W. Harper, et al., Reaction of serine proteases with substituted isocoumarins: Discovery of 3,4-Dichloroisocoumarin, a new general mechanism based serine protease inhibitor, *Biochemistry* 24:1831–1841 (1985).

C. H. Hassal et al., A new class of inhibitors of human leucocyte elastase, *FEBS Lett.* 183:201–205 (1985).

M. A. Hernandez, et al., Effect of the 7-Amino substituent on the inhibitory potency of mechanism-based isocoumarin inhibitors for porcine pancreatic and human neutrophil elastases: A 1.85-Å-X-ray structure of the complex between porcine pancreatic elastase and 7-[(N-Tosylphenylalanyl)amino]-4-chloro-3-methoxyisocoumarin, *J. Med. Chem.* 35:1121–1129 (1992).

A. H. Jackson et al., Sputum sol-phase proteins and elastase activity in patients with systic fibrosis, *J. Respir. Dis.* 65:114–124 (1984).

A. Janoff, Elastase in tissue injury, *Annu. Rev. Med.* 36:207–216 (1985).

A. Janoff, Elastases and emphysema; Current assessment of the protease-antiprotease hypothesis, *Am. Rev. Respir. Dis.* 132:417–433 (1985).

D. H. Kinder et al., Acylamino boronic acids and difluoroborane analogues of amino acids: Potent inhibitors of chymotrypsin and elastase, *J. Med. Chem.* 28:1917–1925 (1985).

A. Krantz et al., Design and synthesis of 4H-3,1-Benzoxazin-4-ones as potent alternate substrate inhibitors of human leukocyte elastase, *J. Med. Chem.* 33:464–479 (1990).

C.-B. Laurell et al., The electrophoretic $\alpha_1$-Antitrypsin deficiency, *Scand. J. Clin. Lab. Invest.* 15:132–140 (1963).

S. Mehdi et al., The inhibition of human neutrophil elastase and cathepsin G by peptidyl 1,2-Dicarbonyl derivatives, *Biochem. Biophys. Res. Commun.* 166:201–205 (1990).

T. A. Merritt et al., Elastase and $\alpha_1$-Proteinase inhibitor activity in tracheal aspirates during respiratory distress syndrome, *J. Clin. Invest.* 72:656–666 (1983).

H. P. Schnebli, Recombinant elastase inhibitors for therapy, *Ann. N.Y. Acad. Sci.* 624:212–218 (1991).

S. K. Shah, et al., Orally active $\beta$-Lactam inhibitors of human leukocyte elastase-1. Activity of 3,3-Diethyl-2-azetidinones, *J. Med. Chem.* 35:3745–3754 (1992).

J. W. Skiles et al., Inhibition of human leukocyte elastase (HLE) by N-substituted peptidyl trifluoromethyl ketones, *J. Med. Chem.* 35:641–662 (1992).

R. A. Stockley et al., Proteinases in chronic lung infection *Ann. N.Y. Acad. Sci.* 624:257–266 (1991).

J. C. Taylor et al., *Pulmonary emphysema and proteolysis,* New York: Academic Press, (1987).

R. A. Wildonger et al., The in vitro and in vivo inhibition of human leukocyte elastase by $\alpha,\alpha$-difluoro-$\beta$-ketoamides, in *Eleventh American Symposium Abstracts,* poster 87, presented at the University of California, San Diego, Jul. 9–14, 1989.

HUMAN LEUKOCYTE ELASTASE (HLE) INHIBITORS, AND RELATED PHARMACEUTICAL COMPOSITIONS AND METHODS OF USE

TECHNICAL FIELD

The present invention relates generally to pharmaceutical agents for inhibiting human leukocyte elastase (HLE) activity, and more particularly relates to certain novel HLE inhibitors. The invention also relates to methods and pharmaceutical compositions for treating disease states associated with elevated levels of HLE.

BACKGROUND

Human leukocyte elastase is a serine protease that is widely dispersed throughout the body and plays an important role in degrading foreign material as part of the body's normal inflammatory response. Prolonged exposure to high levels of HLE has been associated with the onset of such disease states as pulmonary emphysema, adult respiratory distress syndrome (ARDS), chronic bronchitis, cystic fibrosis, rheumatoid arthritis, and atherosclerosis. See, e.g., A. Janoff, *Am. Rev. Respir. Dis.* 132:417–433 (1985); J. C. Taylor et al., *Pulmonary Emphysema and Proteolysis*, New York: Academic Press, 1987; C. -B. Laurell et al., *Scand. J. Clin. Lab. Invest.* 15:132–140 (1963); T. A. Merritt et al., *J. Clin. Invest.* 72:656–666 (1983); R. A. Stockley et al., *Ann. N.Y. Acad. Sci.* 624:257–266 (1991); A. H. Jackson et al., *J. Respir. Dis.* 65:114–124 (1984); L. Eskerot et al., *Adv. Exp. Med. Biol.* 167:335–344 (1984); and A. Janoff, *Annu. Rev. Med.* 36:207–216 (1985). The excessive levels of HLE associated with the aforementioned diseases are believed to be the result of insufficient production of its natural inhibitor, α1-protease inhibitor (α1-PI).

The protease-antiprotease imbalance theory for HLE-related diseases originated from the observation that people inherently deficient in α1-PI develop an accelerated form of emphysema. C.-B. Laurell et al., supra. Environmental oxidants, such as cigarette smoke, have been shown to be able to oxidize a methionine residue of α1-PI that is essential for inhibitory activity (H. Carp et al., *Proc. Natl. Acad. Sci.* 770:2041–2045 (1982). The resulting oxidized α1-PI is orders of magnitude less potent that α1-PI. The chemotactic properties of HLE result in the recruitment of more neutrophils to the site of inflammation. The initial imbalance is amplified by the release of more HLE by the newly recruited neutrophils.

A rational approach to the therapeutic treatment of HLE-related diseases is to reestablish the protease-antiprotease imbalance using exogenously produced inhibitors to HLE. Researchers have developed the proper cloning vectors and have expressed the natural inhibitor α1-PI using recombinant technologies (H. P. Schnebli, *Ann. N.Y. Acad. Sci.* 624:212–218 (1991), and augmentation therapy using α1-PI is being evaluated clinically. This approach has merit in that the therapeutic agent is a naturally occurring substance and is the natural inhibitor for HLE; however, the cost and route of administration used for peptides like α1-PI make this therapy less than desirable.

Several approaches have been investigated for finding low-molecular-weight mechanism-based inhibitors to HLE. Mechanism-based inhibitors are compounds that bind to a specific class of enzyme (e.g., serine proteases) and are processed like the normal substrates; however, during processing the inhibitors react with active site residues and are either released slowly or not at all from the enzymatic cleft. Mechanism-based inactivators, i.e., inhibitors which act irreversibly, are distinctly different from alkylating agents in that inactivators are completely nonreactive until enzymatic processing. The mechanism of HLE action is well understood and as shown in Scheme 1, consists of five major steps. Following initial formation of a Michealis complex, the substrate carboxyl is attacked by the active site serine (Ser-195) to form a tetrahedral intermediate that collapses to form an acylated HLE intermediate (C-terminal cleaved product released). Hydrolysis regenerates the enzyme, releasing the N-terminal cleaved product. In general, mechanism-based inhibitors to HLE either form very stable tetrahedral intermediates or act as alternate substrates for the enzyme, while mechanism-based inactivators of HLE form very stable acylated HLE intermediates that are resistant to hydrolysis.

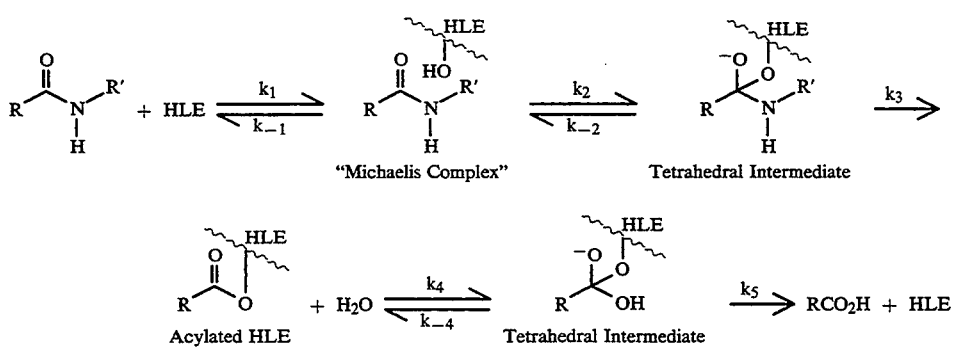

Efforts to develop mechanism-based inhibitors can be divided into two rational design strategies: those directed to development of peptide-derived inhibitors, on the one hand, and those directed to development of non-peptide inhibitors, on the other. In general, peptide-derived inhibitors are designed to resemble the natural substrate sequence and act to form stable tetrahedral intermediates. Examples of peptide-derived inhibitors include boronic acid, aldehyde, α-diketone and α-diketone and α-ketoester, α-fluoro-ketone, and α-ketobenzoxazole derivatives (D. H. Kin der et al., *J. Med. Chem.* 28:1917–1925 (1985); C. H. Hassal et al., *FEBS Lett.* 183:201–205 (1985); S. Mehdi et al., *Biochem. Biophys. Res. Commun.* 166:201–205 (1990); R. A. Wildonger et al., "The in vitro and in vivo inhibition of human leukocyte elastase by α,α-difluoro-β-ketoamides", in *Eleventh American Symposium Abstracts*, poster 87, presented at University of California, San Diego, Jul. 9–14, 1989; J. W. Skiles et al., *J. Med. Chem.* 35:641–662 (1992); and P. D. Edwards, *J. Am. Chem. Soc.* 114:1854–1863 (1992)). A number of nonpeptidic inhibitors have been discovered that are specific for serine proteases and show some selectivity for HLE. These compounds generally act to inactivate the enzyme by forming stable acylated enzyme intermediates. Examples of nonpeptidic mechanism-based inactivators of HLE include ynenol lactones, isocoumarins, cephalosporins, azetidinones, and benzoxazinones. (Copp, L. J. et al., *Biochemistry* 26:169–178 (1987); Harper, J. W. et al., *Biochemistry* 24:7200–7213 (1985); Hernandez, M. A. et al., *J. Med. Chem.* 35:1121–1129 (1992); Harper, J. W. et al., *Biochemistry* 24:1831–1841 (1985); Finke, P. E. et al., *J. Med. Chem.* 35:3731–3744 (1992); Shah, S. K. et al., *J. Med. Chem.* 35:3745–3754 (1992); Krantz A. et al., *J. Med. Chem.* 33:464–479 (1990)).

Most of the reported HLE mechanism-based inhibitors, however, lack plasma solubility, protease stability, and/or enzyme specificity which makes them unsuitable for pharmaceutical development. Accordingly, there remains a need to discover and develop new therapeutic agents that will be effective in treating emphysema and other HLE-related diseases.

The present invention is directed to a novel class of HLE inhibitors which do not have the above-identified disadvantages of the compounds of the prior art. The inhibitors are benzoxazinones substituted at the 6-position as will be discussed in detail below. The effectiveness of these compounds is quite surprising in view of the teaching in the art that substitution at $R_6$ is highly unfavorable and gives rise to compounds which would not be effective HLE inhibitors (see, e.g., A. Krantz et al., *J. Med. Chem.* 33:464–479 (1990)). The novel compounds are potent and specific inhibitors of HLE, and are designed to have greater bioavailability than previous benzoxazinone inhibitors.

OVERVIEW OF RELATED ART

In addition to the publications cited in the preceding section, the following references are of interest as they relate to benzoxazinones and/or HLE inhibitors:

U.S. Pat. No. 4,980,287 to Kokubo et al. designates the 7-position of the benzoxazinone ring as the point of peptide attachment. The disclosed structures are 4H-3,1-benzoxazin-4-ones having the structural formula:

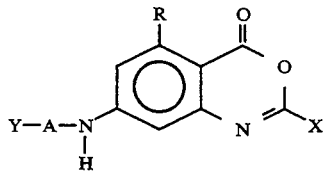

wherein R is a hydrogen atom or alkyl radical, A is an amino acid residue or a peptide having 2 to 3 amino acid residues, Y is a protecting group, and X is alkyl, fluoroalkyl, OR' or NHR' wherein R' is an alkyl radical. These compounds are stated to be inhibitors of serine proteases, particularly human leukocyte elastase.

U.S. Pat. No. 4,657,893 to Krantz et al. describes 4H-3,1-benzoxazin-4-ones having the structural formula

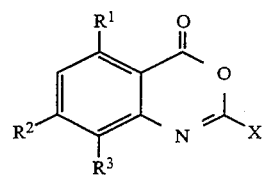

and the pharmaceutically acceptable esters and salts thereof, wherein $R^1$ is hydrogen or lower alkyl, $R^2$ and $R^3$ are each independently hydrogen halo, lower alkyl, hydroxy, lower alkoxy, lower thioalkyl, $-NO_2$, $N(R')_2$, $-NR'COR'$, $-NHCON(R')_2$ or $-NHCOOR'$, and X is a radical such as $-NHR$.

U.S. Pat. No. 4,847,202 to Powers identifies the benzoxazinone ring as important for inhibition of HLE. General serine protease reversible inhibitors are disclosed having the structural formula:

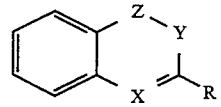

wherein Z is selected from a group-consisting of CO, SO, $SO_2$, CCl, and CF, Y is selected from the group consisting of O, S, NH, and X is selected from the group consisting of N and CH and R is selected from the group consisting of $C_{1-6}$ alkyl, $C_{1-4}$ alkyl containing a phenyl, and $C_{1-6}$ fluoroalkyl.

U.S. Pat. No. 4,745,116 to Krantz et al. is similar to U.S. Pat. No. 4,665,070. 2-Oxy-4H-3,1-benzoxazin-4-ones are disclosed having the structural formula

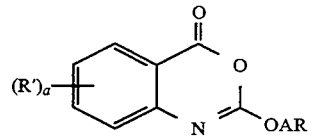

wherein: a is an integer of 1 to 4; A is a bond, or alkylene having one to eight carbon atoms; R is hydrogen, phenyl, imidazolyl, or cycloalkyl having three to six carbon atoms, wherein the phenyl, imidazolyl or cycloalkyl ring is optionally substituted with 1 to 3 substituents independently selected from the group consisting of lower alkyl having one to four carbon atoms, $-N(R^1)_2$, $-NO_2$, halo or lower alkylthio having one to four carbon atoms and, each R' is independently selected from the group consisting of hydroxy, benzyloxy, lower alkyl having one to six carbon atoms, lower alkenyl having two to six carbon atoms, lower alkoxy having one to six carbon atoms, lower alkylthio or halo-lower alkyl having one to six carbon atoms, halo, $-NO_2$, $-N(R^1)_2$, $-NR^1CO_2R^2$, $-NR^1COR^2$, and $-NR^1C(O)N(R^1)_2$, in which each $R^1$ is independently hydrogen or lower alkyl having one to four carbon atoms, or together form a piperidine or a piperazine ring optionally substituted at the ring nitrogen by lower alkyl having one to four carbon atoms or $-CH2CH2OH$; each $R^2$ is independently lower alkyl having one to four carbon atoms, A is an alkylene group if R is hydrogen, or a pharmaceutically acceptable acid addition salt thereof.

Dunn et al. *J. Heterocyclic Chem.* 20:779–780 (1983), and Hedstrom et al., *Biochemistry* 23:1753–1759 (1984), relate to heterocyclic ring structures that inhibit serine proteases.

Spencer et al. *Biochem. Biophys. Res. Commun.* 140:928–931 (1986), examines the importance of 2-position and electron-withdrawing effects of 2-position substituent, and proposes compounds with substituents at 5-, 6-, 7-, and 8-positions, including 6-methyl and 6-methoxy derivatives.

Krantz et al. *J. Med. Chem.* 30:591–597 (1987), examines the effect of replacing hydrogen at the 5-position with alkyl groups, finding that steric hindrance of alkyl slows enzyme deacylation process; i.e. inhibitors become inactivators.

Stein et al. *Biochemistry* 26:4126–4130 (1987), describes the incorporation of amino acids at the 2-position as a way of increasing HLE potency and specificity.

SUMMARY OF THE INVENTION

It is accordingly a primary object of the invention to address the above-mentioned need in the art by providing novel compounds which are potent and specific inhibitors of HLE.

It is another object of the invention to provide pharmaceutical compositions for treating disease states or other physiological conditions associated with serine protease activity.

It is still another object of the invention to provide pharmaceutical compositions for treating disease states or other physiological conditions associated with elevated levels of HLE.

It is a further object of the invention to provide a method for inhibiting serine proteases in animals, comprising administering a therapeutically effective amount of a compound of the invention to the animal undergoing treatment.

It is still a further object of the invention to provide a method for treating disease states or other physiological conditions associated with elevated levels of HLE, comprising administering a therapeutically effective amount of a compound of the invention to the individual undergoing treatment.

Additional objects, advantages and novel features of the invention will be set forth in part in the description which follows, and in part will become apparent to those skilled in the art upon examination of the following, or may be learned by practice of the invention.

In a first embodiment, the invention relates to certain novel compounds which are useful as HLE inhibitors. The novel compounds presently disclosed and claimed possess significant HLE inhibitory activity and may be readily synthesized. The compounds are 4H-3,1-benzoxazin-4-one analogs having the structural formula (I)

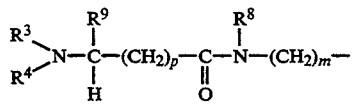

-continued

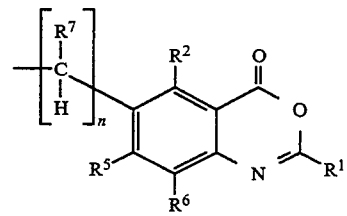

wherein:

$R^1$ is selected from the group consisting of $-CZ_3$, $-OR^{10}$, $-S-R^{11}$ and $-NR^{12}{}_2$ wherein Z is halogen and $R^{10}$ $R^{11}$ and $R^{12}$ are independently selected from the group consisting of hydrogen and lower alkyl;

$R^2$ is selected from the group consisting of hydrogen, halogen and lower alkyl;

$R^3$ is independently selected from the group consisting of hydrogen and lower alkyl;

$R^4$ is selected from the group consisting of hydrogen, $-(CH_2)_q-X$, $-(CH_2)_q-AA_1-NHX$, $-(CH_2)_q-AA_1-AA_2-NHX$, $-(CH_2)_q-AA_1-AA_2-AA_3-NHX$, $-(CH_2)_q-AA_1-AA_2-AA_3-AA_4-NHX$, $-(CH_2)_q-AA_1-AA_2-AA_3-AA_4-AA_5-NHX$ and $-(CH_2)_q-AA_1-AA_2-AA_3-AA_4-AA_5-AA_6-NHK$ wherein q is 0 or 1, $AA_1$, $AA_2$, $AA_3$, $AA_4$, $AA_5$ and $AA_6$ are amino acids, and X is selected from the group consisting of hydrogen, t-butyloxycarbonyl, benzyloxycarbonyl,

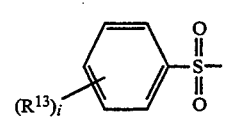

and

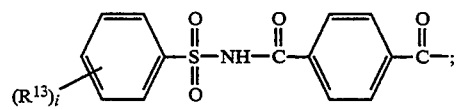

in which the $R^{13}$ are independently selected from the group consisting of halogen, lower alkyl, lower alkoxy, amino and nitro, and i is an integer in the range of 1 to 5 inclusive (and wherein $AA_1$ is bound to the nitrogen atom shown through a carbonyl group, i.e., through a usual peptide linkage, and wherein $AA_2$, $AA_3$, etc., are similarly bound);

$R^5$ and $R^6$ are independently selected from the group consisting of hydrogen, halogen, hydroxy, alkoxy, nitro, primary amino, alkyl-substituted secondary amino, dialkyl-substituted tertiary amino, and —(CO)—$R^{15}$ where $R^{15}$ is hydrogen, hydroxyl, alkyl or halogen;

$R^7$ is selected from the group consisting of hydrogen and lower alkyl, or, when n is 1, $R^7$ and $R^2$ may form a lower alkylene bridge optionally substituted with one to three alkyl groups, or, when m is 0, $R^7$ and $R^8$ may form a lower alkylene bridge optionally substituted with one to three alkyl groups; and $R^8$ and $R^9$ are independently either lower alkyl, monocyclic aryl or monocyclic aralkyl;

m and n are 0, 1 or 2, with the proviso that the sum of m and n is less than or equal to 2.

The invention also relates to pharmaceutical compositions containing one or more of the above compounds in combination with a pharmaceutically acceptable carrier, and further encompasses methods of inhibiting serine proteases comprising administering a therapeutically acceptable amount of a compound of the invention to the individual undergoing treatment. Methods are also provided for treating disease states or other physiological conditions associated with elevated levels of HLE. These methods of treatment involve administration of a composition containing an HLE inhibitor, as defined by formula (I) above, within the context of a dosing regimen effective to achieve the intended therapeutic result. Pulmonary administration of an aerosol formulation is the preferred mode of administration.

DETAILED DESCRIPTION OF THE INVENTION

Definitions and Nomenclature:

Before the present compounds, compositions and methods are disclosed and described, it is to be understood that this invention is not limited to specific reagents or reaction conditions, specific pharmaceutical carriers, or to particular administration regimens, as such may, of course, vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "an HLE inhibitor" includes mixtures of HLE inhibitors, reference to "a pharmaceutical carrier" includes mixtures of two or more such carriers, and the like.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms.

The term "alkylene" as used herein refers to a difunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methylpropylene [—$CH_2$—$CH(CH_3)$—$CH_2$—], hexylene [—$(CH_2)_6$—] and the like. "Lower alkylene" refers to an alkylene group of 1 to 6, more preferably 1 to 4, carbon atoms.

The term "alkenyl" as used herein refers to a branched or unbranched hydrocarbon group of 2 to 24 carbon atoms containing at least one double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. Preferred alkenyl groups herein contain 1 to 12 carbon atoms. The term "lower alkenyl" intends an alkenyl group of one to six carbon atoms, preferably one to four carbon atoms. The term "cycloalkenyl" intends a cyclic alkenyl group of three to eight, preferably five or six, carbon atoms.

The term "alkenylene" refers to a difunctional branched or unbranched hydrocarbon chain containing from 2 to 24 carbon atoms and at least one double bond. "Lower alkenylene" refers to an alkenylene group of 2 to 6, more preferably 2 to 5, carbon atoms.

The term "alkynyl" as used herein refers to a branched or unbranched hydrocarbon group of 2 to 24 carbon atoms containing at least one triple bond, such as ethynyl, n-propynyl, isopropynyl, n-butynyl, isobutynyl, t-butynyl, octynyl, decynyl and the like. Preferred alkynyl groups herein contain 1 to 12 carbon atoms. The term "lower alkynyl" intends an alkynyl group of one to six carbon atoms, preferably one to four carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "aryl" as used herein refers to an aromatic species containing 1 to 5 aromatic rings, either unsubstituted or substituted with 1 or more substituents typically selected from the group consisting of —$(CH_2)_x$—$NH_2$, —$(CH_2)_x$—$COOH$, —$NO_2$, halogen and lower alkyl, where x is an integer in the range of 0 to 6 inclusive as outlined above. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkylene groups have the structure —$(CH_2)_j$—Ar wherein j is an integer in the range of 1 to 24, more typically 1 to 6, and Ar is a monocyclic aryl moiety.

The term "arylene" refers to a difunctional aromatic moiety; "monocyclic arylene" refers to a phenylene group. These groups may be substituted with up to four ring substituents as outlined above.

"Halo" or "halogen" refers to fluoro, chloro, bromo or iodo, and usually relates to halo substitution for a hydrogen atom in an organic compound. Of the halos, chloro and fluoro are generally preferred.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

The term "inhibitor" as used herein is intended to include both reversible enzyme inhibitors and irreversible enzyme inhibitors, i.e., enzyme inactivators.

By the term "effective amount" of an agent as provided herein is meant a nontoxic but sufficient amount of the agent to provide the desired inhibition of HLE activity. As will be pointed out below, the exact amount required will vary from subject to subject, depending on the species, age, and general condition of the subject, the severity of the disease associated with elevated HLE levels, the particular HLE inhibitor and its mode of administration, and the like. Thus, it is not possible to specify an exact "effective amount". However, an appropriate effective amount may be determined by one of ordinary skill in the art using only routine experimentation.

The term "pharmaceutically acceptable" to describe pharmaceutical carriers and the like intends materials which are not biologically or otherwise undesirable, i.e., the material may be administered to an individual along with the selected HLE inhibitor without causing any undesirable biological effects or interacting in a deleterious manner with any of the other components of the pharmaceutical composition in which it is contained.

In describing the location of groups and substituents, the following numbering systems will be employed.

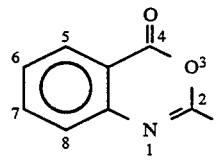

This system is intended to conform the numbering of the 4H-3,1-benzoxazinone nucleus to the convention used by the IUPAC or Chemical Abstracts Service.

The Novel Compounds:

The novel compounds provided herein are those defined by the structural formula (I) above, wherein $R^1$ through $R^7$, m and n are as defined above. Preferred compounds within this generic group are wherein:

$R^1$ is —$OR^{10}$ wherein $R^{10}$ is lower alkyl;

$R^2$ and $R^3$ are independently selected from the group consisting of hydrogen and lower alkyl;

$R^4$ is hydrogen, —X, —$AA_1$-NHX, —$CH_2$-$AA_1$-NHX, -$AA_1$-$AA_2$-NHX or —$CH_2$-$AA_1$-$AA_2$-NHX wherein $AA_1$ and $AA_2$ are selected from the group consisting of neutral, nonpolar amino acids, with exemplary amino acids being valine and alanine, and X is hydrogen, t-butyloxycarbonyl or benzyloxycarbonyl or wherein $R^4$ is

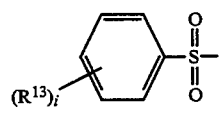

or

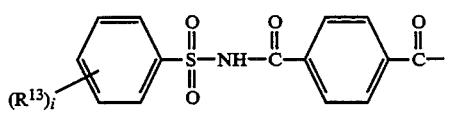

which $R^{13}$ and i are as defined earlier;

$R^5$ and $R^6$ are hydrogen; and $R^8$ and $R^9$ are independently selected from the group consisting of hydrogen and lower alkyl.

Examples of specific preferred compounds are as follows:

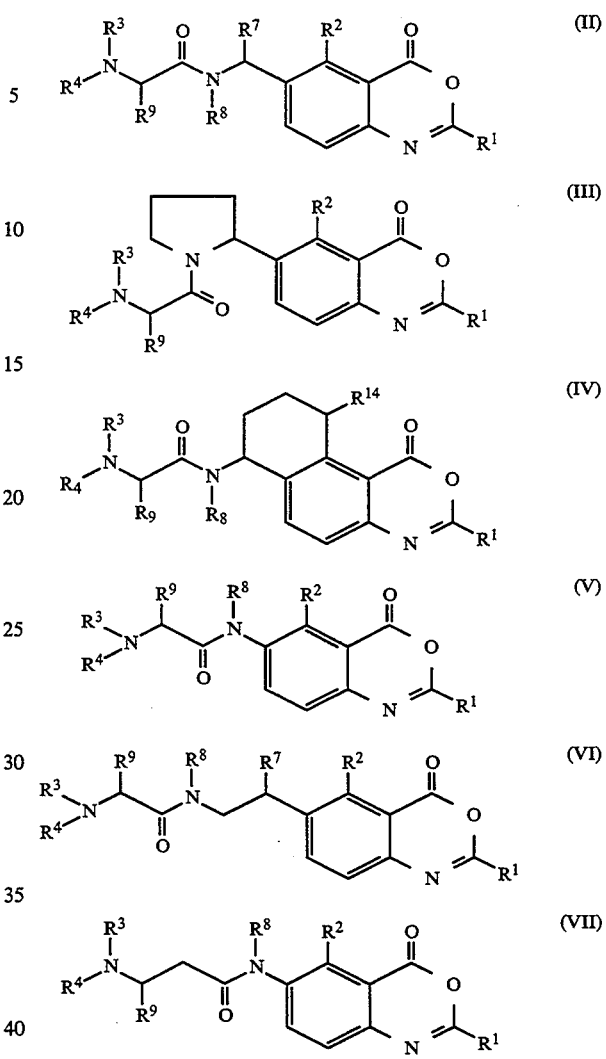

Particularly preferred compounds within the scope of formulae (II) through (VII) are wherein $R^3$ is H and $R^4$ is X.

Utility and Administration:

The compounds of the invention defined by structural formula (I), including the pharmacologically acceptable salts thereof, are useful as serine protease inhibitors, more particularly as HLE inhibitors, and may be conveniently formulated into pharmaceutical compositions composed of one or more of the compounds in association with a pharmaceutically acceptable carrier. *Remington's Pharmaceutical Sciences*, 18th edition, by E. W. Martin (Mack Publ. Co., Easton, Pa. 1990) discloses typical carriers and conventional methods of preparing pharmaceutical compositions which may be used to prepare formulations using the inhibitors of the invention.

The compounds may be administered orally, parenterally (e.g., intravenously), by intramuscular injection, or by intraperitoneal injection, or the like. Pulmonary administration of an aerosol formulation is preferred, particularly for treating emphysema. The amount of active compound administered will, of course, be dependent on the subject being treated, the subject's weight, the manner of administration and the judgment of the prescribing physician. Generally, however, dosage will be in the range of 1 to 500 μg per dose, more typically in the range of 100 to 200 μg per dose, with dosages administered 1 to 3 times daily.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

For pulmonary administration, it is preferred that the drug to be administered be transformed into powder form, combined with a conventional propellant, e.g., a halohydrocarbon such as tetrafluoroethane, trichlorofluoromethane, dichlorofluoromethane, or the like, and administered as an aerosol formulation. The formulation preferably contains surfactants as well, to facilitate and stabilize the suspension or dispersion of drug powder in the propellant. The drug powder will normally constitute about 0.1 to 10 wt. % of the formulation. The solid particle aerosol formulation will typically be administered in one or more unit doses, with dosages as set out above, to provide therapeutic levels of drug.

Process for Preparation:

The compounds of the invention may be prepared in high yield using relatively simple, straightforward methods as exemplified in the experimental section herein.

General routes of synthesis are as follows. Synthesis of various 6-(peptidyl)amino-5-methyl-2-ethoxy-3,1-benoxazin-4-ones is dependent upon generation of the parent compound, 6-amino-5-methyl-2-ethoxy-3,1-benzoxazin-4-one. The parent compound is most effectively prepared using 6-methyl-2-aminobenzoic acid (a commercially available compound) as the starting material. 6-Amino-5-methyl-2-ethoxy-3,1-benzoxazin-4-one can be obtained by hydrogenolysis of the corresponding 6-nitro-5-methyl-2-ethoxy-3,1-benzoxazin-4-one. This latter material is produced by the reaction of 5-nitro-6-methyl-2-aminobenzoic acid with two equivalents of ethyl chloroformate in pyridine, a reaction which produces both the benzoxazinone ring and the 2-ethoxy substituent in one step.

Since nitration of 6-methyl-2-aminobenzoic acid directly would produce a mixture of mononitration and dinitration products, it is preferred that precautions be taken to moderately deactivate the amino functionality to enhance the yield of mononitration product. An aminoacyl (NHCOR) moiety is well known to induce such deactivation because the carbonyl group withdraws some of the electron density away from nitrogen, making those electrons less available for induction into the aromatic ring.

5-Nitro-6-methyl-2-aminobenzoic acid is produced upon hydrolysis of 5-nitro-6-methyl-2-(acyl)aminobenzoic acid. In the present case, the simple acetyl group ($CH_3CO$) may be used to induce the aforementioned deactivation. Thus, the substrate to be hydrolyzed may be 5-nitro-6-methyl-2-acetylaminobenzoic acid. This material can be obtained by fuming nitric acid induced mononitration of 6-methyl-2-acetylaminobenzoic acid, which, in turn, is prepared by reaction of the commercially available material with acetic anhydride. The entire synthetic scheme is outlined in Scheme I and exemplified below.

Once the key intermediate, 6-amino-5-methyl-2-ethoxy-3,1-benzoxazin-4-one, has been prepared, derivatization to make a variety of 6-(peptidyl)amino-5-methyl-2-ethoxy-3,1-benzoxazin-4-one analogs suitable for testing as HLE inhibitors is performed by the coupling of an appropriately N-protected amino acid, or N-protected peptide, with the key intermediate under classical "mixed anhydride" conditions using isobutyl chloroformate and N-methylmorpholine with tetrahydrofuran (THF) as solvent. This sequence is shown in Scheme II using a generalized (N-tertbutoxycarbonyl)amino acid as the representative coupling partner with the benzoxazinone, and is exemplified in the experimental section, below.

Synthesis of the analogous 6-(peptidyl)amino-5-ethyl-2-ethoxy-3,1-benzoxazin-4-ones cannot be prepared in exactly the same manner because the required 6-ethyl-2-aminobenzoic acid is not commercially available. Consequently, an alternate route was developed based upon known isatin chemistry.

Scheme I

-continued

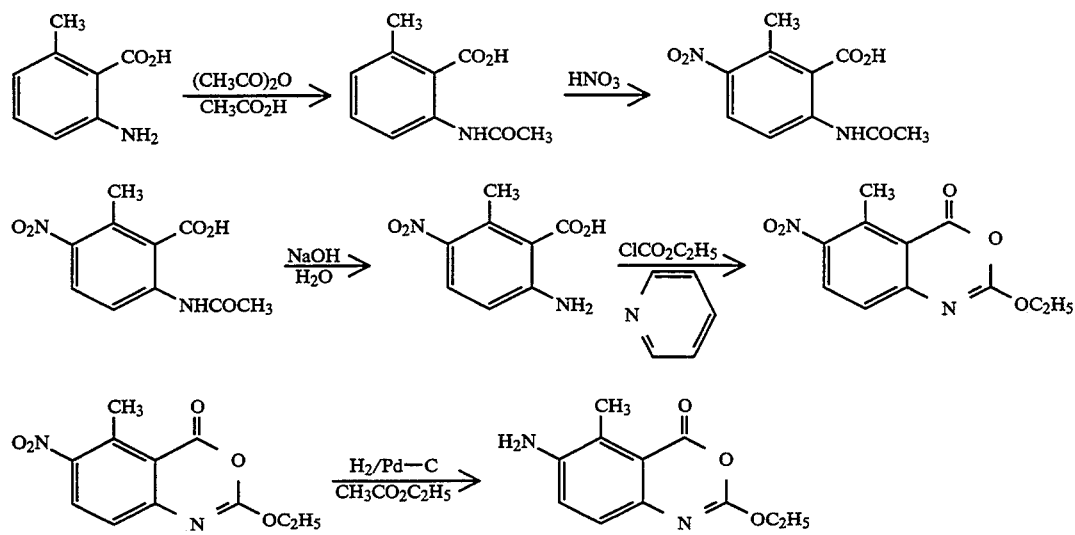

Scheme II

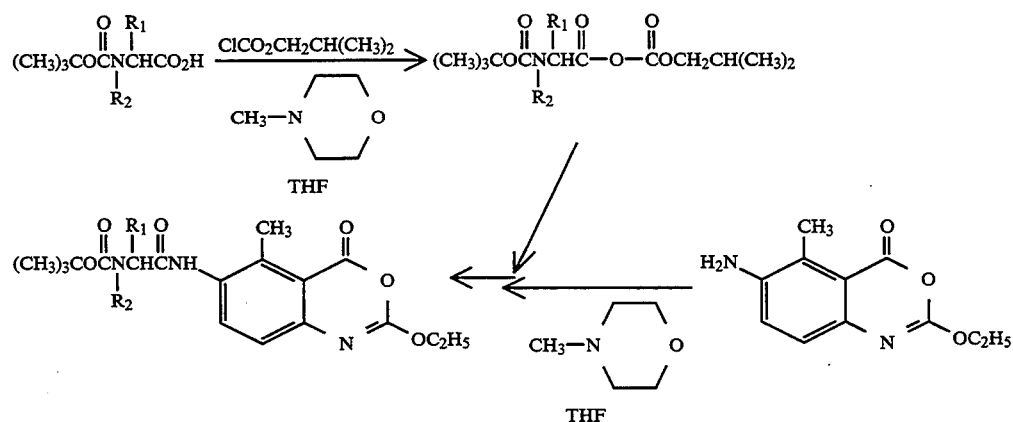

R₁ = alkyl, arylalkyl
R₂ = H, CH₃

Using the commercially available (Aldrich Chemical Company) 3-ethylaniline as starting material, reaction with trichloroacetaldehyde and hydroxylamine produces 3-ethylisonitrosoacetanilide. This product could be cyclized in the presence of sulfuric acid to produce a readily separable mixture of 4-ethylisatin and 6-ethylisatin. Pure 4-ethylisatin could be selectively mononitrated under controlled conditions with fuming nitric acid to provide exclusively 5-nitro-4-ethylisatin. Reaction with hydrogen peroxide under basic conditions forms 5-nitro-6-ethyl-2-aminobenzoic acid. From this point, the synthetic chemistry used can be identical to that used in the 5-methylbenzoxazinone series: formation of the 2-ethoxy-benzoxazinone ring using ethyl chloroformate in pyridine; hydrogenolysis of the 6-nitro to the 6-amino functionality; and mixed anhydride coupling with N-protected amino acids or N-protected peptides. The entire sequence is shown in Schemes III and IV.

Scheme III

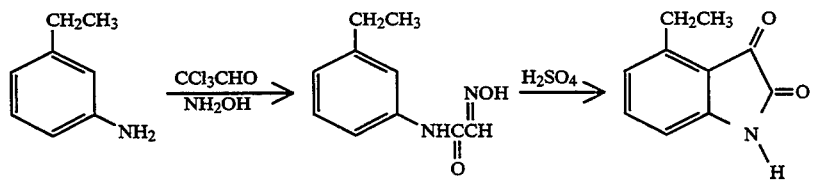

-continued
Scheme III
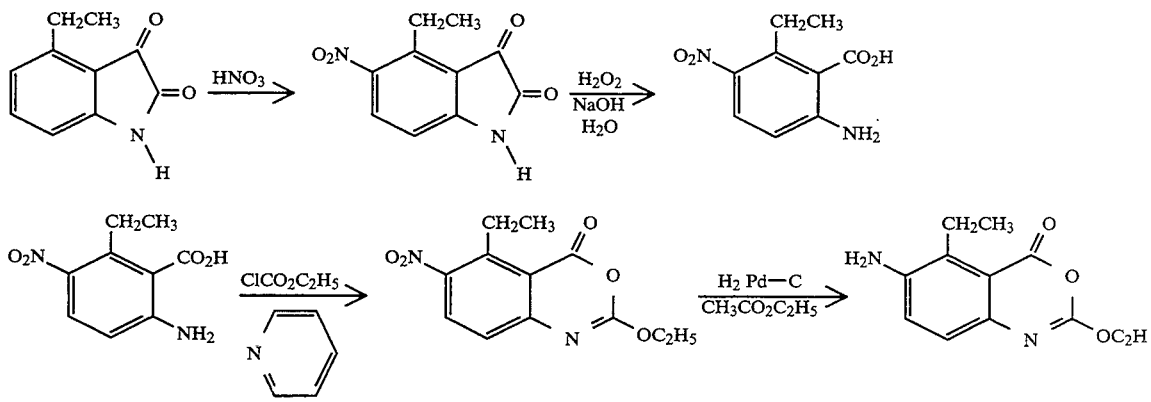
Scheme IV
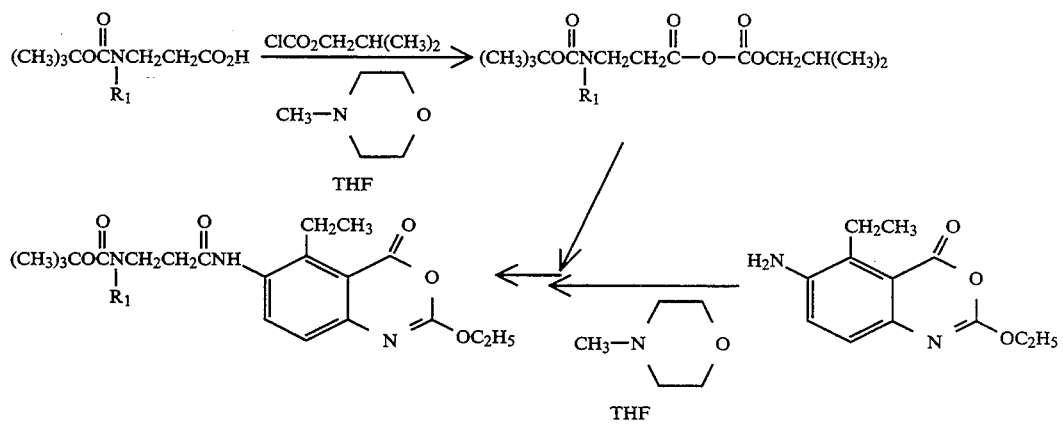
R₁ = H, CH₃
Still an additional synthetic route to those compounds of the invention wherein an —NH— or —NR— moiety is present one carbon atom removed from the aromatic ring is illustrated in Scheme V:
Scheme V
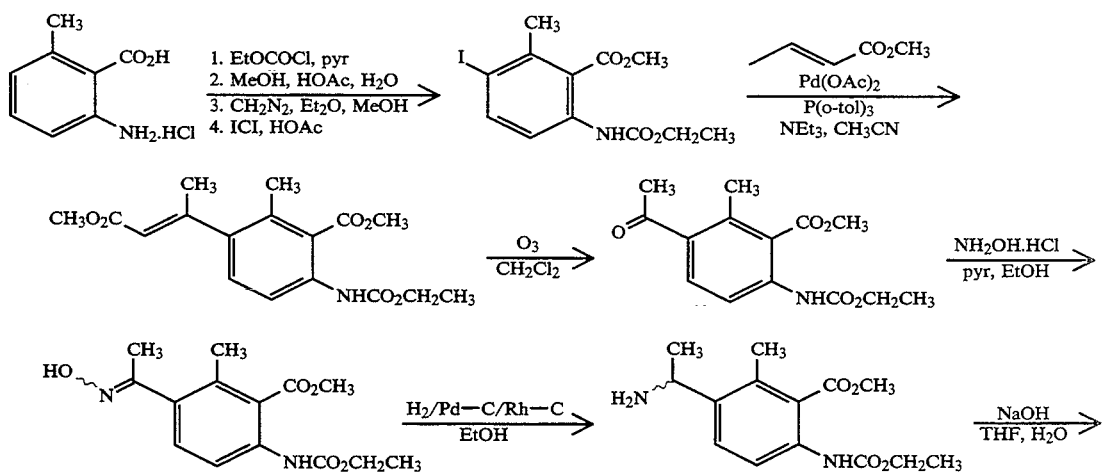

-continued
Scheme V

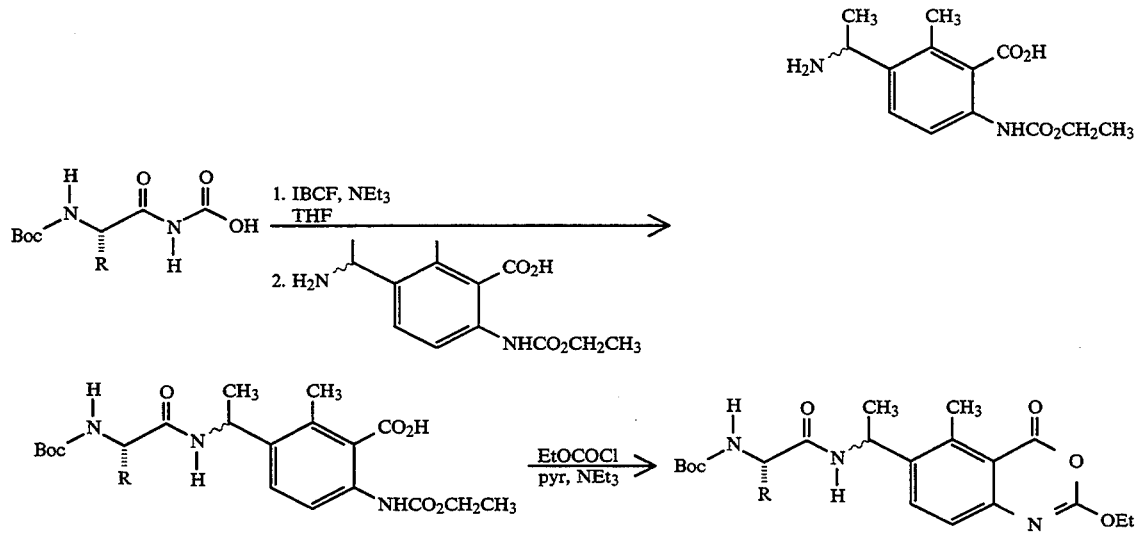

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXPERIMENTAL

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

All solvents were purchased as HPLC grade and, where appropriate, solvents and reagents were analyzed for purity using common techniques. All reactions were routinely conducted under an inert atmosphere of argon, unless otherwise indicated.

Analytical thin-layer chromatography (TLC) was conducted using 250μ silica gel GF and 2.5×10 and 5×20 plates (Analtech). Preparative TLC Was conducted using 2000μ silica gel GF and 20×20 plates. NMR analyses were conducted on a Varian Gemini-300 300 Hz machine and were referenced to chloroform at δ7.27. FTIR spectra were recorded on a Perkin Elmer 1600 Series spectrometer.

SPECIFIC SYNTHETIC RESULTS

Acetylation of commercially available 6-methyl-2-aminobenzoic acid according to the procedure of G. W. Rewcastle, et al., *J. Med. Chem.*, 30:843 (1987), provided 6-methyl-2-acetylaminobenzoic acid (see Theilhacker et al., *Annalen*, 669:85 (1963)). Following the procedures of Theilhacker et al., in the cited reference, this material was first nitrated and then deacetylated to yield, first, 6-nitro-5-methyl-2-acetylaminobenzoic acid, then, 6-nitro-5-methyl-2-aminobenzoic acid, both of which are characterized only by melting point and elemental analysis in the Annalen paper. The generalized procedure of A. Krantz, et al. *J. Med. Chem.*, 33:464 (1990), allowed simultaneous formation of the benzoxazinone ring and placement of the substituent at C-2. Hydrogenation of the nitro functionality to the 6-amino moiety was achieved by the procedure of G. Fenton, et al., *J. Med. Chem.*, 32:265 (1989), to give the key intermediate, 6-amino-5-methyl-2-ethoxy-3,1-benzoxazin-4-one. Fenton reported use of 5% palladium on carbon catalyst, whereas the present synthesis utilized 10% palladium on carbon.

For the 5-ethyl analogs, commercially available 3-ethylaniline was subjected to the standard isatin synthesis procedure as detailed by C. S. Marvel and G. S. Hiers in ORGANIC SYNTHESIS, Collective Volume 1, p.327. Whereas Marvel and Hiers used aniline as the precursor, 3-ethylaniline was taken through this same procedure by B. R. Baker, et al., *J. Org. Chem.*, 17:164 (1951), to generate a mixture of 4-ethylisatin and 6-ethylisatin in an approximate 1:1 ratio, a result duplicated in the present synthetic scheme. Baker et al. also used only melting points and elemental analysis in the characterization of his products. Nitration of 4-ethyl isatin prior to oxidative ring-opening to the substituted anthranilic acid is unique to the present procedure. Following generation of 5-nitro-4-ethylisatin, formation of 5-nitro-6-ethyl-2-aminobenzoic acid using basic hydrogen peroxide followed the procedure given by Baker in the above-cited reference. With the anthranilic acid in hand, the procedures of Krantz and Fenton (supra) were employed to generate, first, 6-nitro-5-ethyl-2-ethoxy-3,1-benzoxazin-4-one, then, 6-amino-5-ethyl-2-ethoxy-3,1-benzoxazin-4-one.

Almost all of the N-protected amino acids which were coupled to the benzoxazinones were commercially available. These included (N-tertbutoxycarbonyl)alanine, (N-tertbutoxycarbonyl)valine, and (N-tertbutoxycarbonyl)β-alanine. The only N-protected amino acid which required synthesis was the known (N-tertbutoxycarbonyl,N-methyl)β-alanine, which was prepared by N-methylation of the parent N-protected amino acid using sodium hydride and methyl iodide according to the procedure of A. Yasui et al., *Int. J. Pept. Prot. Res.* 5:301.

The N-protected single amino acids were reacted with either 6-amino-5-methyl-2-ethoxy-3,1-benzoxazin-4one or 6-amino-5-ethyl-2-ethoxy-3,1-benzoxazin-4-one using standard 'mixed anhydride' procedures involving isobutyl chloroformate and N-methylmorpholine in tetrahydrofuran solvent.

EXAMPLE 1

This example describes preparation of 6-amino-5-methyl-2-ethoxy-3,1-benzoxazin-4-one, using the synthetic procedure shown in Scheme I.

(a.) Preparation of 6-methyl-2-acetylaminobenzoic acid:

A suspension of 15.2 g (100 mmoles) of 6-methyl-2-aminobenzoic acid (obtained from the Aldrich Chemical Company, Inc., Milwaukee Wis.) in 150 mL of glacial acetic acid was heated in a water bath to promote homogeneity. Acetic anhydride, 15 mL (159 mmole), was added and the resultant solution kept in the hot water bath for 40 minutes. Upon cooling to near room temperature, the dark solution was poured over crushed ice. When all ice had melted, the pale beige solid which had separated was collected and air-dried. 16.4 g (85% yield) 6-methyl-2-acetylaminobenzoic acid was obtained. NMR(DMSO-$d_6$): 2.00(s,3H), 2.33(s,3H), 7.05(d,1H,J=7.5 Hz), 7.29(t,1H,J=7.8 Hz), 7.41(d,1H,J=7.8 Hz), 9.60(bs,1H). MS(m/z): 193(M+).

(b.) Preparation of 5-nitro-6-methyl-2-acetylaminobenzoic acid:

A beaker containing 35 mL (833 mmoles) of 90% fuming nitric acid was cooled in an ice-water bath. 16.4 g (85 mmoles) of 6-methyl-2-acetylaminobenzoic acid was added in small aliquots over a period of 10 minutes. The solid dissolved immediately upon addition and the solution turned dark. The mixture was stirred, while cooling, for 60 minutes. Upon pouring the solution over crushed ice, a solid precipitated. NMR analysis clearly showed only partial reaction completion as NH protons were observable at 9.61 ppm, indicating starting material, and at 9.83 ppm, indicating product.

All isolated material was resubjected to the nitration procedure, with the following change in conditions: the solid was added to fuming nitric acid while stirring at room temperature rather than in a cooling bath, and after addition was completed, stirring was continued for 90 minutes before pouring the solution over ice. A beige solid was obtained with NMR analysis showing only an NH proton at 9.81 ppm. The solid can be recrystallized from ethanol-water if desired. 10.3 g (51% yield) 5-nitro-6-methyl-2-acetyl-aminobenzoic acid was obtained. NMR(DMSO-$d_6$): 2.07(s,3H), 2.41(s,3H), 7.70(d,1H,J=9.0 Hz), 7.98(d,1H,J=9.0 Hz), 9.81(s,1H). MS(m/z): 238(M+).

(c.) Preparation of 5-nitro-6-methyl-2-aminobenzoic acid:

A solution of 10.2 g (43 mmoles) of 5-nitro-6-methyl-2-acetylaminobenzoic acid in 100 mL of 2M NaOH was heated to reflux for two hours. The resultant red solution was allowed to cool to near room temperature, then transferred to a beaker sitting in an ice bath. The solution was slowly acidified with 2N HCl to a pH of approximately 4–5 when a voluminous yellow solid separated out. In all, approximately 110 mL of 2N HCl was added. The collected yellow solid was dried in a vacuum oven for 3 hours at 75 degrees. 4.0 g (48% yield) 5-nitro-6-methyl-2-aminobenzoic acid was obtained. NMR(DMSO-$d_6$): 2.45 (s,3H), 3.35(bs,2H), 6.68(d,1H,J=9.0 Hz), 7.86(d,1H,J=9.0 Hz). MS(m/z): 196(M+).

(d.) Preparation of 6-nitro-5-methyl-2-ethoxy-3,1-benzoxazin-4-one:

A solution of 4.0 g (20.4 mmoles) of 5-nitro-6-methyl-2-aminobenzoic acid in 50 mL of dry pyridine was cooled in an ice-water bath under inert atmosphere. Ethyl chloroformate (Aldrich), 10 mL (105 mmoles), was added dropwise over a 15 minute period. A mild exotherm was observed and a solid separated from solution immediately upon addition. The suspension was stirred at room temperature under inert atmosphere overnight. Approximately half the pyridine was removed in vacuo, and the residual mixture poured over ice. The precipitated solid was collected and air-dried. 4.0 g (79% yield) 6-nitro-5-methyl-2-ethoxy-3,1-benzoxazin-4-one was obtained. NMR (DMSO-$d_6$): 1.37(t,3H,J=7.2 Hz), 2.71(s,3H), 4.50(q,2H,J=7.2 Hz), 7.40(d,1H, J=9.0 Hz), 8.19(d,1H,J=9.0 Hz). IR(nujol): 1765 cm$^{-1}$ (lactone carbonyl). MS(m/z): 250(M+).

(e.) Preparation of 6-amino-5-methyl-2-ethoxy-3,1-benzoxazin-4-one:

A solution of 4.0 g (16 mmoles) of 6-nitro-5-methyl-2-ethoxy-3,1-benzoxazin-4-one in 65 mL ethyl acetate was transferred to a Parr bottle. 1.0 g (0.94 mmoles) 10% Pd/C catalyst (obtained from Matheson, Coleman & Bell) was added. The sample was hydrogenated on a Parr shaker at ambient room temperature and 1 atm pressure for 5 hours. The catalyst was removed by filtration through a pad of Celite. The filtrate was concentrated in vacuo to produce a bright yellow solid. There was obtained 2.5 g (71% yield) of 6-amino-5-methyl-2-ethoxy-3,1-benzoxazin-4-one. NMR (DMSO-$d_6$): 1.33(t,3H,J=6.9 Hz), 2.46(s,3H), 4.36(q,2H,J=6.9 Hz), 5.24(bs,2H), 7.05(d,1H,J=8.4 Hz), 7.14(d,1H,J=8.4 Hz). IR(nujol): 1743 cm$^{-1}$ (lactone carbonyl). MS(m/z): 220(M+).

EXAMPLE 2

Preparation of 6-(N-tert-butyloxycarbonyl-$\beta$-alanyl)amino-5-methyl-2-ethoxy-4H-3,1-benzoxazin-4-one This example describes the preparation of 6-(N-tert-butyloxycarbonyl-$\beta$-alanyl)-amino-5-methyl-2-ethoxy-4H-3,1-benzoxazin-4-one, using the synthetic procedure illustrated in Scheme II.

A solution of 189 mg (1.0 mmoles) of N-tert-butyloxycarbonyl-$\beta$-alanine (BACHEM) in 2.0 mL of dry tetrahydrofuran (distilled from sodium metal and benzophenone) was cooled to −5° C. under an inert atmosphere. 220 μL (2.0 mmoles) of N-methyl-morpholine (Aldrich) and 130 μL (1.0 mmoles) of isobutyl chloroformate (Aldrich) were added sequentially. A white solid separated immediately. After stirring the mixture in the cooling bath for 15 minutes, 221 mg (1.0 mmoles) 6-amino-5-methyl-2-ethoxy-3,1-benzoxazin-4-one, and 9 mL of dry tetrahydrofuran was quickly added.

The resultant suspension was stirred in the cold for another 60 minutes, then allowed to warm to room temperature with continued stirring for two days. Ethyl acetate was added and the mixture extracted 3× with saturated NaCl solution. The organic phase was dried with MgSO$_4$ and concentrated in vacuo to produce a yellow solid.

Column chromatography on silica gel (bed dimensions: 37 cm×3 cm) using methylene chloride:ethyl acetate (3:2) as eluant gave 112 mg (29% yield) 6-(N-tert-butyloxycarbonyl-β-alanyl)-amino-5-methyl-2-ethoxy-3,1-benzoxazin-4-one as a pale yellow solid. NMR(CDCl$_3$): 1.44(t,3H,J=6.9 Hz), 1.44(s,9H), 2.67(s,3H), 2.69(t,2H), 3.52(bt,2H), 4.49(q,2H,J=6.9 Hz), 5.11(bs, 1H), 7.27(d,1H,J=8.7 Hz), 7.52(bs,1H), 7.91(d,1H,J=8.7 Hz).

EXAMPLE 3

This example describes preparation of 6-(N-tert-butyloxycarbonyl-N-methyl-β-alanyl)-amino-5-methyl-2-ethoxy-3,1-benzoxazin-4-one and 6-(N-tert-butyloxycarbonyl-β-alanyl)-amino-5-ethyl-2-ethoxy-3,1-benzoxazin-4-one, using the synthetic procedures illustrated in Scheme II.

(a.) Preparation of N-tert-butyloxycarbonyl-N-methyl-β-alanine:

A solution of 1.89 g (10.0 mmoles) of N-tert-butyloxycarbonyl-β-alanine dissolved in 25 mL of dry tetrahydrofuran (distilled from sodium metal and benzophenone) was cooled in an ice-methanol bath under an inert atmosphere. Methyl iodide, 11.36 g (80.0 mmoles), was added, followed by the addition of 1.60 g (40.1 mmoles) of sodium hydride (as a 60% dispersion in mineral oil) in small portions over a 10 minute period. Hydrogen gas evolution was immediate, the solution turned yellow, and a precipitate formed which made magnetic stirring difficult. An additional 10 mL of dry tetrahydrofuran was added to facilitate stirring.

The mixture was kept cold for 60 minutes, then warmed to room temperature and stirred under inert atmosphere for 21 hours. The yellow color disappeared, but the precipitate remained. The mixture was cautiously quenched by slowly transferring it to a beaker containing ethyl acetate and water. All solids dissolved in this biphasic mixture, which was transferred to a separatory funnel for layer separation. The ethyl acetate layer was extracted 2× with 5% NaHCO$_3$ and the aqueous washes were combined with the original water phase.

The aqueous phase was carefully acidified with 10% HCl and re-extracted 2× with fresh ethyl acetate. The organic extracts were combined, washed 1× with saturated NaCl solution, dried over MgSO$_4$, and concentrated in vacuo to obtain a viscous orange oil.

Column chromatography on silica gel (bed dimensions: 20 cm×3 cm) using chloroform:methanol (95:5) as eluant gave 1.68 g (83% yield) of N-tert-butyloxycarbonyl-N-methyl-β-alanine as a light yellow oil. NMR(CDCl$_{13}$): 1.38(s,9H), 2.50(t,2H,J=6.9 Hz), 2.81(s,3H), 3.43(t,2H,J=6.9 Hz), 10.16(bs,1H). IR(nujol): 1707 cm$^{-1}$ (acid carbonyl); 1666 cm$^{-1}$ (urethane carbonyl).

(b.) Preparation of 6-(N-tert-butyloxycarbonyl-N-methyl-β-alanyl)-amino-5-methyl-2-ethoxy-3,1-benzoxazin-4-one:

The procedure of Example 2 was followed using a final reaction mixture of: 110 mg (0.54 mmoles) N-tert-butyloxycarbonyl-N-methyl-β-alanine, 110 μL (1.0 mmoles) N-methylmorpholine, 70 μL (0.54 mmoles) isobutyl chloroformate, 120 mg (0.54 mmoles) 6-amino-5-methyl-2-ethoxy-3,1-benzoxazin-4-one, and 8 mL dry tetrahydrofuran. The reaction mixture was stirred at room temperature for five days.

Column chromatography on silica gel (bed dimensions: 22 cm×3 cm) using methylene chloride:ethyl acetate (3:2) as eluant gave 58 mg (29% yield) of 6-(N-tert-butyloxycarbonyl-N-methyl-β-alanyl) -amino-5-methyl-2-ethoxy-3,1-benzoxazin-4-one as a pale yellow solid. NMR(CDCl$_3$): 1.44(t,3H,J=7.2 Hz), 1.45(s,9H), 2.67(s.3H), 2.72(t,2H, J=6.3 Hz), 2.92(s,3H), 3.64(t,2H, J=6.3 Hz), 4.49(q,2H,J=7.2 Hz), 7.26(d,1H,J=8.7 Hz), 7.85(d,1H,J=8.7 Hz), 8.40(bs,1H).

(c.) Preparation of 6-(N-tert-butyloxycarbonyl-β-alanyl)-amino-5-ethyl-2-ethoxy-3,1-benzoxazin-4-one:

The procedure of Example 2 was followed using a final reaction mixture of: 95 mg (0.50 mmoles) N-tert-butyloxycarbonyl-β-alanine, 110 μL (1.0 mmoles) N-methylmorpholine 65 μL (0.50 mmoles) isobutyl chloroformate, 117 mg (0.50 mmoles) 6-amino-5-ethyl-2-ethoxy-3,1-benzoxazin-4-one, and 7 mL dry tetrahydrofuran. The reaction mixture was stirred at room temperature for three and one-half days.

Column chromatography on silica gel (bed dimensions: 22 cm×3 cm) using methylene chloride:ethyl acetate (3:2) as eluant gave 41 mg (20% yield) of 6-[N-tert-butyloxycarbonyl-β-alanyl]amino-5-ethyl-2-ethoxy-3,1-benzoxazin-4-one as a pale yellow solid. NMR(CDCl$_3$): 1.20(t,3H,J=7.5 Hz), 1.44(t,3H,J=7.2 Hz), 1.44(s,9H), 2.68(t,2H), 3.19(q,2H,J=7.5 Hz), 3.51(m,2H), 4.49(q,2H,J=7.2 Hz), 5.12(bs,1H), 7.29(d,1H,J=8.7 Hz), 7.44(bs,1H), 7.99(d,1H,J=8.7 Hz).

EXAMPLE 4

This example describes preparation of 6-amino-5-ethyl-2-ethoxy-3,1-benzoxazin-4-one using the synthetic procedures illustrated in Scheme III.

(a.) Preparation of 3-ethylisonitrosoacetanilide:

A solution composed of 50.0 g (320 mmoles) chloral hydrate (Aldrich), 70.0 g (490 mmoles) sodium sulfate, and 800 mL water were stirred at room temperature in a 2 liter round bottom flask. Added was a solution of 33.0 g (270 mmoles) 3-ethylaniline (Aldrich) dissolved in a mixture of 60 mL of concentrated hydrochloric acid and 140 mL water. Finally, a solution of 60.0 g (860 mmoles) of hydroxylamine hydrochloride dissolved in 200 mL of water was added to the flask. The resultant homogeneous solution was heated to boiling in a water bath for 45 minutes. Cooling the solution to room temperature caused separation of a fluffy solid. There was obtained 27.3 g (53% yield) of 3-ethylisonitrosoacetanilide. NMR(CD$_3$OD): 1.21(t,3H,J=7.5 Hz), 2.62(q,2H,J=7.5 Hz), 6.97(d,1H,J=7.8 Hz), 7.21(t,1H,J=7.8 Hz), 7.43(d,1H,J=7.8 Hz), 7.47(s, 1H), 7.58(s,1H). MS(m/z): 192(M+).

(b.) Preparation of 4-ethylisatin and 6-ethylisatin:

A 250 mL round bottom flask containing 100 mL of concentrated sulfuric acid was heated in a water bath with the internal temperature maintained at 50 degrees. Added in small portions was 17.3 g (90 mmoles) of 3-ethylisonitrosoacetanilide over a 45 minute period at such a rate as to control the internal solution temperature between 60–70 degrees. After complete addition, the resultant red-black solution was warmed to 80–85 degrees and maintained at that temperature for 75 minutes. After cooling to room temperature, the solution was poured over crushed ice. The aqueous solution was extracted five times with chloroform. The organic extracts were combined, dried over MgSO$_4$, filtered, and concentrated in vacuo. There was obtained an orange solid, which was a combination of both 4-ethylisatin and 6-ethylisatin.

The orange solid was taken up in 50 mL of 10% NaOH. Addition of glacial acetic acid until a pH of approximately 4 was obtained induced crystallization of an orange, fluffy solid. There was obtained 2.1 g (13% yield) of 4-ethylisatin. NMR(CDCl$_3$) 1.23(t,3H,J=7.5 Hz), 2.97(q,2H,J=7.5 Hz), 6.76(d,1H,J=7.8 Hz), 6.93(d,1H,J=8.4 Hz), 7.43(t,1H,J=7.8 Hz), 8.80(bs,1H). MS(m/z): 175(M+).

The red-orange acetic acid filtrate was further acidified to a pH of approximately 1 with concentrated hydrochloric acid to produce a powdery orange solid. 2.1 g (13% yield) 6-ethylisatin was obtained. NMR(CDCl$_3$): 1.27(t,3H, J=7.5 Hz), 2.69(q,2H,J=7.5 Hz), 6.78(s,1H), 6.94(d,1H, J=7.8 Hz), 7.53(d,1H,J=7.8 Hz), 8.49(bs,1H).

(c.) Preparation of 5-nitro-4-ethylisatin:

A beaker containing 15 mL of 90% fuming nitric acid was cooled in an ice-water bath. 2.1 g (12 mmoles) 4-ethylisatin was added in small portions over a five-minute period. The resultant red-orange solution was stirred while in the ice-water bath for 5 minutes, then warmed to room temperature and stirred for another 10 minutes. A yellow solid precipitated immediately when this solution was poured over crushed ice. 1.4 g (52% yield) 5-nitro-4-ethylisatin was obtained. NMR(CDCl$_3$): 1.29(t,3H, J=7.5 Hz), 3.11(q,2H,J=7.5 Hz), 7.11 (d,1H,J=8.7 Hz), 8.27 (d,1H,J=8.7 Hz), 9.46(bs,1H). MS(m/z): 220(M+).

(d.) Preparation of 5-nitro-6-ethyl-2-aminobenzoic acid:

To a solution of 1.0 g (4.5 mmoles) of 5-nitro-4-ethylisatin in 8.0 mL of 5% NaOH was slowly added 1.25 mL (11 mmoles) of 30% hydrogen peroxide over 10 minutes. A mild exotherm was detectable. The solution was stirred at room temperature for 60 minutes, then poured over crushed ice. The solution was acidified with 10% HCl until the 'cloud point'. The suspension was extracted 3× with ethyl acetate. The combined organic extracts were washed 1× with water, dried over MgSO$_4$, and concentrated in vacuo. There was obtained a dark oil, which upon standing at room temperature, became an orange-rust colored solid. 0.78 g (82% yield) of 5-nitro-6-ethyl-2-aminobenzoic acid was obtained. NMR(DMSO-d$_6$): 1.16(t,3H,J=7.2 Hz), 2.88(q,2H,J=7.2 Hz), 3.34(bs,2H), 6.66(d,1H,J=9.3 Hz), 7.84(d,1H,J=9.3 Hz). MS(m/z): 210(M+).

(e.) Preparation of 6-nitro-5-ethyl-2-ethoxy-3,1-benzoxazin-4-one:

A solution of 1.3 g (6.2 mmoles) of 5-nitro-6-ethyl-2-aminobenzoic acid in 40 mL of dry pyridine was cooled in an ice-water bath under inert atmosphere. Ethyl chloroformate, 2 mL (21 mmoles), was added dropwise over a five-minute period. A mild exotherm was observed and a solid separated from solution immediately upon addition. The suspension was stirred in the ice-water bath for 60 minutes, then warmed to room temperature and stirred under inert atmosphere overnight. Approximately half the pyridine was removed in vacuo, and the residual mixture was poured over ice. The precipitated solid, an orange brown color, was collected and air-dried. 0.76 g (47% yield) 6-nitro-5-ethyl-2-ethoxy-3,1-benzoxazin-4-one was obtained. NMR(CDCl$_3$): 1.36(t,3H,J=7.5 Hz), 1.47(t,3H,J=7.2 Hz), 3.27(q,2H,J=7.2 Hz), 4.56(q,2H, J=7.5 Hz), 7.36(d,1H,J=9.0 Hz), 7.98(d,1H,J=9.0 Hz). MS(m/z): 282(M+ +H$_2$O).

(f.) Preparation of 6-amino-5-ethyl-2-ethoxy-3,1-benzoxazin-4-one:

A solution of 0.75 g (2.8 mmoles) 6-nitro-5-ethyl-2-ethoxy-3,1-benzoxazin-4-one in 35 mL ethyl acetate was transferred to a Parr bottle. 0.40 g (0.38 mmoles) of 10% Pd/C catalyst was added. The sample was hydrogenated on a Parr shaker at ambient temperature and 1 atm pressure for 3 hours. The catalyst was removed by filtration through a pad of Celite. The filtrate was concentrated in vacuo to produce a bright yellow solid. There was obtained 0.58 g (86% yield) of 6-amino-5-ethyl-2-ethoxy-3,1-benzoxazin-4-one. NMR(CDCl$_3$): 1.22 (t,3H,J=7.5 Hz), 1.42(t,3H,J=7.2 Hz), 3.14(q,2H,J=7.5 Hz), 4.44(q,2H,J=7.2 Hz), 7.09(d,1H,J=8.7 Hz), 7.14(d,1H,J=8.7 Hz). MS(m/z): 234(M+).

EXAMPLE 5

This example illustrates preparation of 6-(N-tert-butyloxycarbonyl-N-methyl-$\beta$-alanyl)-amino-5-ethyl-2-ethoxy-3,1-benzoxazin-4-one, as illustrated in Scheme IV.

The procedure of Example 2 was followed using a final reaction mixture of: 102 mg (0.50 mmoles) N-tert-butyloxycarbonyl-N-methyl-$\beta$-alanine, 110 $\mu$L (1.0 mmoles) N-methylmorpholine, 65 $\mu$L (0.50 mmoles) isobutyl chloroformate, 118 mg (0.50 mmoles) 6-amino-5-ethyl-2-ethoxy-3,1-benzoxazin-4-one, and 6 mL of tetrahydrofuran. The reaction mixture was stirred at room temperature for five days.

Column chromatography on silica gel (bed dimensions: 22 cm×3 cm) using methylene chloride:ethyl acetate (3:1) as eluant gave 19 mg (3% yield) 6-(N-tert-butyloxycarbonyl-N-methyl-$\beta$-alanyl)-amino-5-ethyl-2-ethoxy-3,1-benzoxazin-4-one as a pale yellow solid. NMR(CDCl$_3$): 1.20(t,3H,J=7.5 Hz), 1.43(t,3H,J=7.2 Hz), 1.45(s,9H), 2.70(t,2H,J=6.9 Hz), 2.92(s,3H), 3.18(q,2H,J=7.5 Hz), 3.62(t,2H,J=6.9 Hz); 4.48(q,2H,J=7.2 Hz); 7.06(bs,1H); 7.28(d,1H,J=8.7 Hz), 8.02(d,1H,J=8.7 Hz).

EXAMPLE 6

This example describes preparation of 6-(N-4-methylbenzenesulfonyl-N-methyl-$\beta$-alanyl)-amino-5-ethyl-2-ethoxy-4H-3,1-benzoxazin-4-one using the synthetic procedures illustrated in Scheme III.

(a.) Preparation of (N-methyl)$\beta$-alanine, trifluoroacetic acid salt:

To a round bottom flask containing 1.02 g (5.0 mmoles) (N-tertbutoxycarbonyl,N-methyl)$\beta$-alanine was added a solution of 5 mL (6.5 mmoles) trifluoroacetic acid dissolved in 6 mL of methylene chloride. The resultant solution was stirred at room temperature under inert atmosphere for 60 minutes. The solution was concentrated in vacuo and the residue transferred dropwise into an Erlenmeyer flask containing 50 mL of anhydrous diethyl ether. Stirring at room temperature produced a white solid precipitate, which was collected and air-dried. 0.84 g (77% yield) (N-methyl)$\beta$-alanine, trifluoroacetic acid salt, was obtained as a white solid. NMR(DMSO-d$_6$): 2.57(s,3H); 2.60–2.65(t,2H,J=6.9 Hz); 3.07–3.12(t,2H,J=6.9 Hz). IR(nujol): 2500–2700 cm$^{-1}$(NH$_2$+ stretches); 1728 cm$^{-1}$ (acid carbonyl); 1670 cm$^{-1}$ (acid carbonyl).

(b.) Preparation of (N-4-methylbenzenesulfonyl, (N-methyl)$\beta$-alanine, N,N-dicyclohexylmanine salt:

To a round bottom flask containing 0.84 g (3.9 mmoles) of (N-methyl)$\beta$-alanine, trifluoroacetic acid salt and 0.49 g (4.0 mmoles) N,N-dimethylaminopyridine (Aldrich) was added a mixture of 25 mL of methylene chloride and 3 mL N,N-dimethylformamide. The salt appeared to remain insoluble. The mixture was cooled in an ice-water bath under inert atmosphere. After the addition of 6 mL (43.0 mmoles) of triethylamine, the mixture remained heterogeneous.

A solution of 0.75 g (3.9 mmoles) of p-toluenesulfonyl chloride (Aldrich) dissolved in a mixture of 15 mL of methylene chloride and 2 mL of N,N-dimethylformamide was added dropwise to the suspension. Addition was complete in 30 minutes, after which stirring in the cold was continued for an additional 60 minutes. During this time, all solids dissolved leaving a colorless, homogeneous solution. The solution was warmed to room temperature and stirred under inert atmosphere for an additional 20 hours.

The solution was acidified to a pH of approximately 1 with 10% HCl, and the layers separated after mixing. The organic phase was washed 2× with additional 10% HCl, 3× with saturated NaCl solution, dried over MgSO$_4$, and concentrated in vacuo to obtain a pale yellow oil.

The oil was redissolved in 35 mL of anhydrous diethyl ether. While stirring, N,N-dicyclohexylamine (Aldrich) as added dropwise in excess. A white solid precipitated from solution, which was collected and air-dried. 1.24 g (73% yield) of (N-4-methylbenzenesulfonyl, (N-methyl)$\beta$-alanine, N,N-dicyclohexylamine (DCHA) salt, was obtained. NMR(DMSO-d$_6$): 1.02–1.86(m,18H); 2.25–2.30(t,2H,J=7.5 Hz); 2.40(s,3H); 2.63(s,3H); 2.68–2.74(m.,4H); 3.07–3.12(t,2H,J=7.5 Hz); 7.42–7.44(d,2H,J=7.8 Hz); 7.62–7.65(d,2H,J=7.8 Hz). IR(nujol): 2400–2700 cm$^{-1}$(NH$_2^+$ stretches); 1623 cm$^{-1}$ (acid carbonyl); 1335 cm$^{-1}$ and 1153 cm$^{-1}$ (symmetric and asymmetric SO$_2$ stretches).

(c.) Preparation of 6-(N-4-methylbenzenesulfonyl-N-methyl-$\beta$-alanyl)-amino-5-ethyl-2-ethoxy-4H-3,1-benzoxazin-4-one:

The procedure of Example 2 was followed using a final reaction mixture of 207 mg (0.80 mmoles) (N-4-methylbenzenesulfonyl, N-methyl)$\beta$-alanine (obtained by acidification of 450 mg (1.03 mmoles) of the DCHA salt with 12N HCl, followed by extraction with ethyl acetate and concentration of the organic phase in vacuo), 180 µL (1.64 mmoles) N-methylmorpholine, 105 µL (0.81 mmoles) isobutyl chloroformate, 190 mg (0.81 mmoles) 6-amino-5-ethyl-2-ethoxy-3,1-benzoxazin-4-one, and 8 mL dry tetrahydrofuran. The reaction mixture was stirred at room temperature for one and one-half days.

Column chromatography on a silica gel (bed dimensions 22 cm×3 cm) using methylene chloride:ethyl acetate (3:1) as eluant gave 28 mg (7% yield) 6-[(N-4-methylbenzenesulfonyl,N-methyl)methylbenzenesulfonyl,N-methyl)$\beta$-alanyl] amino-5-ethyl-2-ethoxy-3,1-benzoxazin-4-one as a golden yellow solid. NMR(CDCl$_3$): 1.26–1.31(t,3H,J=7.2 Hz); 1.45–1.49(t,3H,J=7.2 Hz); 2.47(s,3H); 2.81–2.85(t,2H,J=6.6 Hz); 2.85(s,3H); 3.20–3.27(q,2H,J=7.2 Hz); 3.36–3.41(t,2H,J=6.6 Hz); 4.49–4.56 (q,2H,J=7.2 Hz); 7.27–7.30(d,1H,J=8.7 Hz); 7.36–7.39(d,2H,J=8.1 Hz); 7.70–7.73(d,2H,J=8.1 Hz); 7.82(s,1H); 7.93–7.95(d,1H,J=8.7 Hz).

EXAMPLE 7

This example describes preparation of 6-[1-(N-tert-butyloxycarbonyl-L-valyl)-aminoethyl]-2-ethoxy-5-methyl-4H-3,1-benzoxazin-4-one using the synthetic procedures illustrated in Scheme V.

(a.) Preparation of methyl 2-ethyloxycarbonylamino-5-iodo-6-methyl benzoate:

To 15 g (80 mmoles) 2-amino-6-methyl benzoic acid hydrochloride (Aldrich) in 100 mL pyridine at 0° C. was added 17 mL (177 mmoles) of ethylchloroformate and the resulting mixture was stirred overnight at room temperature. The reaction was concentrated in vacuo to give a mixture of ring-open and ring-closed products.

The residue was taken up in 50 mL of aqueous methanol (1:1) and 20 mL of acetic acid and heated on a steam bath to open ring-closed products. The reaction was concentrated in vacuo and then dissolved in 200 mL of a mixture diethyl ether and methanol (4:1). A 150 mL portion of 0.5M diazomethane was added to the solution, and the resulting mixture was stirred for 20 min, the excess diazomethane (generated from Diazaid ®, Aldrich Chemical Company, Inc.) was quenched using 10% acetic acid in ether, and the reaction was concentrated in vacuo.

The resulting syrup was dissolved in 200 mL of acetic acid, 14 g (86 mmoles) of iodinemonochloride (Aldrich) was added and the reaction was stirred for 2 days at 50° C. The reaction mixture was poured into 1.5 L of an ice-brine slush and this was stirred until a gummy solid precipitated. The residue was dissolved in methylene chloride, dried over MgSO$_4$, and evaporated to a gum.

Column chromatography on silica gel (bed dimensions: cm×cm) using methylene chloride:hexane (1:1) as the eluant gave 14.5 g (50% yield) methyl 2-ethyloxycarbonylamino-5-iodo-6-methyl benzoate, melting point 70°–71° C. TLC (methylene chloride/hexane, 1:3) R$_f$=0.41. NMR (CDCl$_3$): 1.29(t,3H), 2.44(s,3H), 3.93(s,3H), 4.19(q,2H), 7.66(d,1H,J$_{3,4}$=9.2 Hz), 7.84(d,1H, J$_{3,4}$=9.2 Hz), 8.08(s,1H).

(b.) Preparation of methyl 2-ethyloxycarbonyl-5-(2-methyloxy-carbonyl-1-methyl-ethylenyl)-6-methyl benzoate:

A mixture of 14.5 g (40 mmoles) methyl 2-ethyloxycarbonylamino-5-iodo-6-methyl benzoate, 6 g (60 mmoles) methyl crotonate (Aldrich), 4.5 g (49.4 mmoles) triethylamine, 180 mg (0.8 mmole) palladium-(II)acetate (Aldrich), and 980 mg (3.2 mmoles) tri-O-tolylphosphine (Aldrich) in 100 mL of acetonitrile was heated with magnetic stirring at 110°–120° C. for 18 hr using a 250 mL glass pressure bomb. The reaction was evaporated to dryness, then dissolved in methylene chloride, filtered to remove palladium, washed successively with 0.1N HCl and water, dried over MgSO$_4$, filtered, and evaporated to dryness.

Column chromatography on silica gel (bed dimensions: cm×cm) with chloroform, followed by crystallization from methylene chloride: hexane gave 5.0 g (40% yield) of methyl 2-ethyloxycarbonyl-5-(2-methyloxycarbonyl-1-methyl-ethylenyl)-6-methyl benzoate. TLC (methylene chloride) R$_f$=0.44. NMR (CDCl$_3$) 1.39(t,3H), 2.37(s,3H), 2.49(d,3H,J=1.5 Hz), 4.26(s,3H), 4.29(q,2H), 4.33(s,3H), 5.84(q,1H,J=1.5 Hz), 7.22(d,1H,J$_{3,4}$=8.6 Hz), 8.05(d,1H,J$_{3,4}$=8.6 Hz).

Anal. calc'd for C$_{17}$H$_{21}$NO$_6$: C, 60.88; H, 6.31; N, 4.18. Found: C, 60.97; H, 6.31; N, 4.32.

(c.) Preparation of methyl 2-ethyloxycarbonyl-5-(2-methyloxycarbonyl-1-methyl-ethylenyl)-6-methyl benzoate:

A solution of 5 g (14.9 mmoles) of methyl 2-ethyloxycarbonyl-5-(2-methyloxycarbonyl-1-methylethylenyl)-6-methyl benzoate in methylene chloride was cooled to −30° C. and ozonized oxygen gas was passed into the solution until a permanent blue color was obtained. The reaction was cooled to −60° C., flushed with argon to remove excess ozone, and 2 mL of dimethyl sulfide added. The reaction was warmed to −10° C. and stirred for one hour, followed by stirring at room temperature for an additional hour. The solution was evaporated to a glassy residue.

Column chromatography on silica gel (bed dimensions: cm×cm) with chloroform gave 3.85 g (87% yield) of methyl 5-acetyl-2-ethyloxycarbonyl-6-methyl benzoate. TLC (methylene chloride) $R_f$=0.27. NMR (CDCl$_3$) 1.32(t,3H), 2.48(s,3H), 2.58(s,3H), 3.88(s,3H), 4.14(q,2H), 7.62(d,1H,$J_{3,4}$=8.8 Hz), 8.00(d,1H,$J_{3,4}$=8.8 Hz).

(d.) Preparation of methyl 5-(1-isonitrosoethyl)-2-ethyloxy-carbonylamino-6-methyl benzoate:

To 3.5 g (12.5 mmoles) methyl 5-acetyl-2-ethyloxycarbonyl-6-methyl benzoate in a 100 mL mixture of pyridine and ethanol (1:1) was added 3.5 g (50.0 mmoles) hydroxylamine hydrochloride (Aldrich), and the resulting solution was heated on a steam bath for one hour. Upon cooling a gummy precipitate started to form. The mixture was poured into 250 mL of saturated brine to complete the precipitation. The aqueous layer was decanted, the precipitated gum dissolved in chloroform, washed with saturated brine, dried over MgSO$_4$, filtered, and evaporated to dryness to give 3.2 g (87% yield) of methyl 5-(1-isonitroso-ethyl)-2-ethyloxycarbonylamino-6-methyl benzoate as the syn- and anti-isomers, melting point 85°-90° C. TLC (methylene chloride) $R_f$0.37. NMR (CDCl$_3$) 1.29(t,3H), 2.12,2.17(2s,3H), 2.28,2.32(2s,3H), 3.92(s,3H), 4.19(q,2H), 7.14,7.28(2d,1H), 7.97,8.04 (2d,1H), 8.35,8.47(2s,1H).

(e.) Preparation of methyl 5-(1-aminoethyl)-2-ethyloxy-carbonylamino-6-methyl benzoate:

To 3.0 g (10.2 mmoles) methyl 5-(1-isonitrosoethyl)-2-ethyloxycarbonylamino-6-methyl benzoate in a mixture of 50 mL of 95% ethanol and 1 mL of acetic acid was added 500 mg of 10% Pd/C (MCB) and 100 mg 10% Rh/C (Alfa products, Thiokol) and the resulting mixture placed under a hydrogen atmosphere and shaken for 9 days. The mixture was filtered and evaporated to dryness. The residue was dissolved in chloroform, washed with saturated sodium bicarbonate followed by saturated brine, dried over MgSO$_4$, filtered and evaporated to dryness.

Column chromatography on silica gel (bed dimensions: cm×cm) with ethyl acetate to elute unreacted oxime followed by methanol to elute the product amine. The methanolic solution was evaporated to a glass, the residue was dissolved in chloroform, filtered through Celite and evaporated to give 1.3 g (45% yield) of methyl 5-(1-aminoethyl)-2-ethyloxycarbonyl-6-methyl benzoate. TLC (chloroform/methanol, 95:5) Rf=0.20. NMR (CDCl$_3$) 1.30(t,3H), 1.36(d,3H,J=6.7 Hz), 2.33(s,3H), 3.87(s,3H), 4.20(q,2H), 7.59(d,1H,$J_{3,4}$=8.9 Hz) 7.90(d,1H,$J_{3,4}$=8.9 Hz).

(f.) Preparation of 5-(1-aminoethyl)-2-ethyloxyarbonylamino-6-methyl benzoate:

Methyl 5-(1-aminoethyl)-2-ethyloxycarbonyl-6methyl benzoate (1.2 g; 4.3 mmoles) was dissolved in a mixture of 50 mL of THF and 50 mL of 0.7N sodium hydroxide and stirred at room temperature for 3 days. The THF was evaporated and the aqueous solution neutralized with 35 mL of 1N hydrochloric acid. The aqueous solution was evaporated to dryness. The residue was taken up in DMF, the NaCl precipitate filtered off, and the product precipitated using a mixture of ether and water. The precipitate was filtered and air-dried to give 510 mg (45% yield) of 5-(1-aminoethyl)-2-ethyloxycarbonylamino-6-methyl benzoate. NMR (DMSO-d$_6$) 1.21(t,3H) 1.48(d,3H,J=6.6 Hz), 2.33(s,3H), 4.08(q,2H), 4.52(q,1H,J=6.6 Hz), 7.28(d,1H,$J_{3,4}$=8.8 Hz), 7.77(d,1H,$J_{3,4}$=8.8 HZ).

(g.) Preparation of 6-[1-(N-tert-butyloxycarbonyl-L-valyl)-aminoethyl]-2-ethyloxy-5-methyl-4H-3,1-benzoxazin-4-one:

To 115 mg (0.55 mmoles of Boc-L-valine (BACHEM) in 10 mL of dry THF was added 165 μL (1.2 mmoles) triethylamine. After stirring for 0.5 hours at room temperature, the solution was cooled to 0° C. and 78 μL (0.6 mmoles) of isobutylchloroformate was added. The mixture was stirred for 1 hour at 0° C. before adding a solution of 130 mg (0.5 mmoles) 5-(1-aminoethyl)-2-ethyloxyarbonylamino-6-methyl benzoate in 5 mL dry THF. The reaction was allowed to come to room temperature and stirred for 18 hours. The reaction was evaporated to dryness, dissolved in chloroform, washed with 0.1N hydrochloric acid followed by saturated brine, dried over MgSO$_4$, filtered and evaporated to dryness to give 140 mg (78% yield) of crude intermediate.

The residue was dissolved in a solution containing 5 mL of pyridine and 1 mL of triethylamine. Ethylchloroformate (0.5 mL; 4.6 mmoles) was added to the vessel and the resulting solution heated to 50° C. for 2 hours. The mixture was poured into 50 mL of a briny slush and extracted with three 50 mL portions of chloroform. The combined extracts were washed with 0.1N hydrochloric acid followed by saturated brine, dried over MgSO$_4$, filtered and evaporated to dryness.

The product was crystallized three times from methylene chloride/hexane (1:1) to give 45 mg (20% yield) of 6-[1-(N-tert-butyloxycarbonyl-L-valyl)-aminoethyl]-2-ethyloxy-5-methyl-4H-3,1-benzoxazin-4-one isomer A. TLC (methylene chloride/acetone, 9:1) $R_f$=0.59. NMR (CDCl3) 0.89(d,3H), 0.91(d,3H), 1.44(t,3H), 1.44(s,9H), 1.46(d,3H,J=6.8 Hz), 2.10(m,1H), 2.80(s,3H), 3.81(dd,1H), 4.49(q,2H), 5.00(bd,1H), 5.40(m,1H), 6.30(d,1H), 7.25(d,1H,$J_{7,8}$=8.4 Hz), 7.61(d,1H,$J_{7,8}$=8.4 Hz). MS 447(M+). Anal. calc'd for C$_{23}$H$_{33}$N$_3$O$_6$: C, 61.72; H, 7.43; N, 9.39. Found: C, 61.47; H, 7.24; N, 9.20.

The mother liquor from the first crystallization was loaded on a preparative TLC plate and developed using methylene chloride/hexane (1:5) . Recovery gave 10 mg (4.5%) 6-[1-(N-tert-butyloxycarbonyl-L-valyl)-aminoethyl]-2-ethyloxy-5-methyl-4H-3,1-benzoxazin-4-one isomer B. NMR (CDCl$_3$) 0.93(d,3H), 0.97(d,3H), 1.43(t,3H), 1.44(s,9H), 1.45(d,3H), 2.13(m,1H), 2.78(s,3H), 3.80(dd,1H), 4.98(bd,1H), 5.38(m,1H), 6.41(bd,1H), 7.20(d,1H,$J_{7,8}$=8.5 Hz), 7.59(d,1H,$J_{7,8}$=8.5 Hz). MS 447(M+).

EXAMPLE 8

This example describes preparation of 6-[1-(N-tert-butyloxycarbonyl-L-alanyl)-aminoethyl]-2-ethyloxy-5-methyl-4H-3,1-benzoxazin-4-one, using the synthetic procedures illustrated in Scheme V.

To 50 mg (0.27 mmoles) of N-tert-butyloxycarbonyl-L-alanine (BACHEM) in 10 mL of dry THF was added 83 μL (0.60 mmoles) of triethylamine. After stirring for 0.5 hours at room temperature, the solution was cooled to 0° C. and 39 μL (0.30 mmoles) of isobutylchloroformate was added. The mixture was stirred for 1 hour at 0° C. before adding a solution of 65 mg (0.25 mmoles) 5-(1-aminoethyl)-2-ethyloxyarbonylamino-6-methyl benzoate in 5 mL dry THF. The reaction was allowed to come to room temperature and stirred for 18 hours. The reaction was evaporated to dryness, dissolved in chloroform, washed with 0.1N hydrochloric acid followed by saturated brine, dried over MgSO4, filtered and evaporated to dryness to give 80 mg (73% yield) of crude intermediate.

The residue was dissolved in a solution containing 5 mL of pyridine and 1 mL of triethylamine. Ethylchloroformate (0.5 mL; 4.6 mmoles) was added to the vessel and the resulting solution heated to 50° C. for 2 hours. The mixture was poured into 50 mL of a briny slush and extracted with three 50 mL portions of chloroform. The combined extracts were washed with 0.1N hydrochloric acid followed by saturated brine, dried over MgSO4, filtered and evaporated to dryness.

| Enzyme | Substrate |
|---|---|
| Elastase (human neutrophil) (HLE) | methoxy—Suc—Ala—Ala—Pro—Val—pNA |
| Elastase (porcine pancreatic) (PPE) | Suc—Ala—Ala—Ala—pNA |
| Cathepsin-G (human neutrophil) (CATH) | Suc—Ala—Ala—Pro—Phe—pNA |
| α Chymotrypsin (bovine pancreatic) (CHY) | Suc—Gly—Gly—Phe—pNA |
| Trypsin (bovine pancreatic) (TRP) | Bz—Arg—pNA |

Preparation of 6-[1-(N-tert-butyloxycarbonyl-L-valyl)aminoethyl]-2-ethyloxy-5-methyl-4H-3,1-benzoxazin-4-one ("SR 12144B") was prepared as described above in Example 7. PIPES, HEPES, and BRIJ 35 for buffers were obtained from Calbiochem.

The following assay conditions were used to determine inhibition of each enzyme by SR 12144B.

| Enz. | [E] | [S] | [SR 12144B] | Buffer | % DMSO |
|---|---|---|---|---|---|
| HLE | 0.75 nM | 31.7 uM | 30 → 7.5 nM | 25 mM HEPES, 1M NaCl 0.1% BRIJ 35 pH 6.5 | 2.7 |
| CATH | 50 nM | 1 mM | 10 → 1 μM | 0.1M HEPES, 0.5M NaCl pH 6.5 | 9.0 |
| PPE | 50 nM | 1 mM | 10 → 1 μM | .05MK2HPO4/K2HPO4 pH 7.5 | 9.0 |
| CHY | 100 nM | 0.4 uM | 10 → 3 μM | (Same as PPE) | 9.0 |
| TRP | 50 nM | 0.2 mM | 10 → 3 μM | (Same as PPE) | 9.0 |

Preparative TLC using chloroform followed by crystallization for methylene chloride/hexane gave 21 mg (20%) 6-[1-(N-tert-butyloxycarbonyl-L-alanyl)aminoethyl]-2-ethyloxy-5-methyl-4H-3,1-benzoxazin-4-one as a mixture of two isomers. TLC (methylene chloride/acetone 95:5) Rf=0.33. NMR (CDCl3) (integrations based on two isomers being present in 1:1 ratio as indicated by HPLC) 1.33(d,6H), 1.44(t,6H), 1.45(s,18H), 1.45(d,6H), 2.79(s,6H), 4.13(m,2H), 4.49(q,4H), 5.37(m,2H), 5.86(bd,1H), 5.96(bd,1H), 6.65(bd,1H), 6.78(bd,1H), 7.21(d,1H,J7,8=8.7 Hz), 7.25(d,1H,J7,8=8.6 Hz), 7.58(d,1H,J7,8=8.7 Hz), 7.61(d,1H,J7,8=8.6 Hz). MS 419 (M+).

EXAMPLE 9

Biological Testing
MATERIALS AND METHODS:

Enzymes and their substrates, listed below, were obtained from Calbiochem.

Enzyme-inhibitor mixtures were assayed by the progress curve method described by Stein et al. (Stein et al., *Biochemistry* 26:4126–4130 (1987). SR 12144B, previously dissolved in DMSO, was added to the buffer/substrate solution prior to addition of the enzyme. After a 20 second mixing, a fifteen minute timecourse was recorded following the formation of nitroaniline at 410 nM. A Cary-3 spectrophotometer with cuvette holders at a controlled 25° C. was used to record progress curves for at least four inhibitor concentrations for each enzyme. Controls without SR 12144B were routinely run at the same time. Enzyme and substrate concentrations were chosen to obtain pseudo first order conditions for the entire timecourse, with uninhibited enzyme maintaining a constant rate of product formation for longer than the fifteen minute sampling time.

Additional compounds within the scope of the invention were evaluated using the progress curve method of Stein et al. to determine the kinetic constants $k_{on}$, $k_{off}$ as well as the $pK_i$ and relative selectivity for HLE over other serine proteases. Results are set forth in Tables 1 and 2.

TABLE 1

KINETIC CONSTANTS FOR NOVEL BENZOXAZINONE-BASED INHIBITORS OF HLE

| Example | $k_{on}$ (M$^{-1}$ sec$^{-1}$) | $k_{off}$ (sec$^{-1}$) | $pK_i$ |
|---|---|---|---|
| 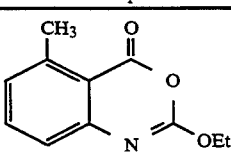 positive control | 140,110 | 0.000072 | 9.29 |

TABLE 1-continued
KINETIC CONSTANTS FOR NOVEL BENZOXAZINONE-BASED INHIBITORS OF HLE
| Example | $k_{on}$ ($M^{-1} sec^{-1}$) | $k_{off}$ ($sec^{-1}$) | $pK_i$ |
|---|---|---|---|
| 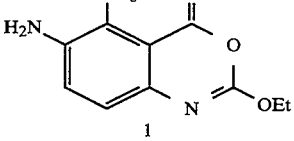 1 | 750,000 | 0.000023 | 10.84 |
| 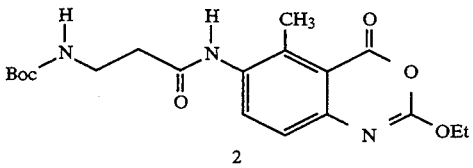 2 | 365,000 | 0.000404 | 8.96 |
| 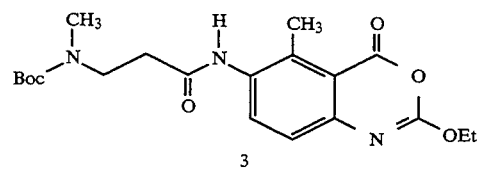 3 | 320,000 | 0.000420 | 8.88 |
| 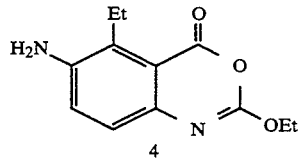 4 | 470,000 | 0.000047 | 10.0 |
| 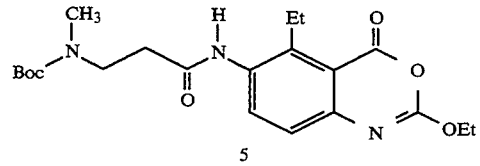 5 | 281,000 | 0.000030 | 9.97 |
| 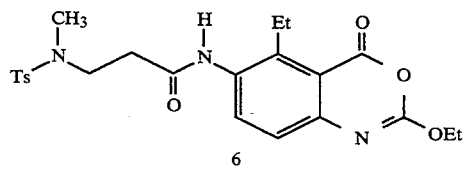 6 | 745,000 | 0.000069 | 10.03 |
| 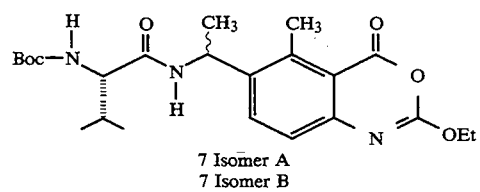 7 Isomer A | 304,000 | 0.000018 | 10.23 |
| 7 Isomer B | 1,100,000 | 0.000016 | 10.84 |
| 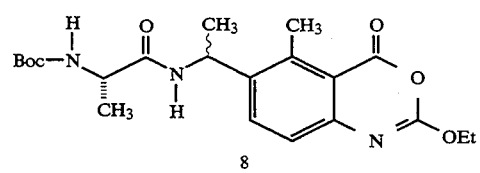 8 | 520,000 | 0.000017 | 10.48 |
| positive control | 140,110 | 0.000072 | 9.29 |
| 1 | 750,000 | 0.000023 | 10.84 |
| 2 | 365,000 | 0.000404 | 8.96 |
| 3 | 320,000 | 0.000420 | 8.88 |
| 4 | 470,000 | 0.000047 | 10.0 |
| 5 | 281,000 | 0.000030 | 9.97 |
| 6 | 745,000 | 0.000069 | 10.03 |
| 7 Isomer A | 304,000 | 0.000018 | 10.23 |

TABLE 1-continued
KINETIC CONSTANTS FOR NOVEL BENZOXAZINONE-BASED INHIBITORS OF HLE

| Example | $k_{on}$ (M$^{-1}$ sec$^{-1}$) | $k_{off}$ (sec$^{-1}$) | $pK_i$ |
|---|---|---|---|
| 7 Isomer B | 1,100,000 | 0.000016 | 10.84 |
| 8 | 520,000 | 0.000017 | 10.48 |

TABLE 2
RELATIVE SELECTIVITY OF NOVEL INHIBITORS FOR HLE OVER OTHER SERINE PROTEASES

| Example | Enzyme | $k_{obs}$/[I] Enzyme (M$^{-1}$sec$^{-1}$) | $k_{obs}$/[I] HLE / $k_{obs}$/[I] Enzyme |
|---|---|---|---|
| 2 | HLE | 365,000 | 1 |
|   | Cathepsin G | 460 | 790 |
|   | Trypsin | 200 | 1830 |
|   | PPE | 2860 | 130 |
|   | Chymotrypsin | 3500 | 100 |
| 6 | HLE | 745,000 | 1 |
|   | Cathepsin G | 340 | 2190 |
|   | Trypsin | 80 | 9312 |
|   | PPE | 3451 | 220 |
|   | Chymotrypsin | 11,900 | 60 |
| 7 Isomer B | HLE | 1,100,000 | 1 |
|   | Cathepsin G | 967 | 1140 |
|   | Trypsin | 1,550 | 710 |
|   | PPE | 967 | 1140 |
|   | Chymotrypsin | 2,570 | 430 |

We claim:

1. A compound having the structural formula (I)

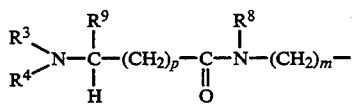

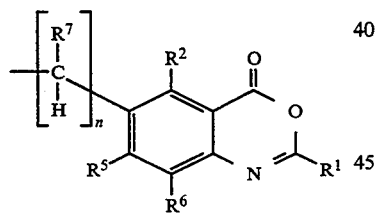

wherein:

$R^1$ is selected from the group consisting of —$CZ_3$, —$OR^{10}$, —S—$R^{11}$ and —$NR^{12}_2$ wherein Z is halogen and $R^{10}$, $R^{11}$ and $R^{12}$ are independently selected from the group consisting of hydrogen and lower alkyl;

$R^2$ is selected from the group consisting of hydrogen, halogen and lower alkyl;

$R^3$ is independently selected from the group consisting of hydrogen and lower alkyl;

$R^4$ is selected from the group consisting of hydrogen, —(CH$_2$)$_q$-X, —(CH$_2$)$_q$-AA$_1$-NHX, —(CH$_2$)$_q$-AA$_1$-AA$_2$-NHX, —(CH$_2$)$_q$-AA$_1$-AA$_2$-AA$_3$-NHX, —(CH$_2$)$_q$-AA$_1$-AA$_2$-AA$_3$-AA$_4$-NHX, —(CH$_2$)$_q$-AA$_1$-AA$_2$-AA$_3$-AA$_4$-AA$_5$-NHX and —(CH$_2$)$_q$-AA$_1$-AA$_2$-AA$_3$-AA$_4$-AA$_5$-AA$_6$-NHX wherein q is 0 or 1, AA$_1$, AA$_2$, AA$_3$, AA$_4$, AA$_5$ and AA$_6$ are amino acids, and X is selected from the group consisting of hydrogen, t-butyloxycarbonyl, benzyloxycarbonyl,

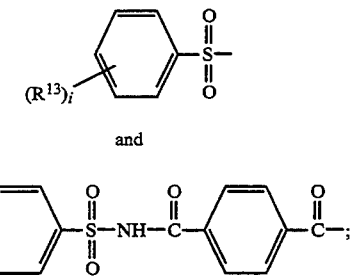

in which the $R^{13}$ are independently selected from the group consisting of halogen, lower alkyl, lower alkoxy, amino and nitro, and i is an integer in the range of 1 to 5 inclusive;

$R^5$ and $R^6$ are independently selected from the group consisting of hydrogen, halogen, hydroxy, alkoxy, nitro, primary amino, alkyl-substituted secondary amino, dialkyl-substituted tertiary amino, and —(CO)—$R^{15}$ where $R^{15}$ is hydrogen, hydroxyl, alkyl or halogen;

$R^7$ is selected from the group consisting of hydrogen and lower alkyl, or, when n is 1, $R^7$ and $R^2$ may form a lower alkylene bridge optionally substituted with one to three alkyl groups, or, when m is 0, $R^7$ and $R^8$ may form a lower alkylene bridge optionally substituted with one to three alkyl groups;

$R^8$ and $R^9$ are independently either lower alkyl, monocyclic aryl or monocyclic aralkyl;

p is 0 or 1; and m and n are 0, 1 or 2, with the proviso that the sum of m and n is less than or equal to 2.

2. The compound of claim 1, wherein $R^4$ is —X.

3. The compound of claim 2, wherein X is t-butyloxycarbonyl.

4. The compound of claim 1, wherein $R^5$ and $R^6$ are hydrogen.

5. The compound of claim 2, wherein $R^5$ and $R^6$ are hydrogen.

6. The compound of claim 1, wherein n is 1 and $R^7$ and $R^2$ are linked together to form an n-propylene bridge.

7. The compound of claim 1, wherein m is 0 and $R^7$ and $R^2$ are linked together to form an n-propylene bridge.

8. The compound of claim 1, having the structural formula

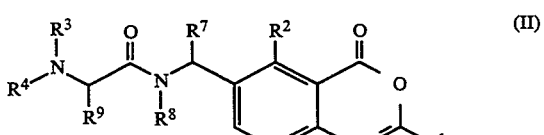

wherein $R^1$ and $R^2$ are lower alkyl.

9. The compound of claim 1, having the structural formula

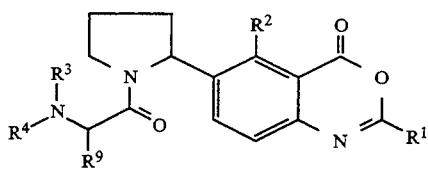
(III)

wherein R¹ and R² are lower alkyl.

10. The compound of claim 1, having the structural formula

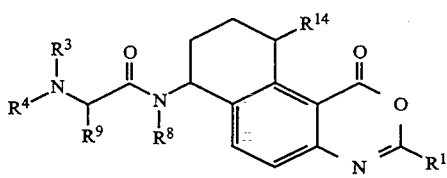
(IV)

wherein R¹, R² and R¹⁴ are lower alkyl.

11. The compound of claim 1, having the structural formula

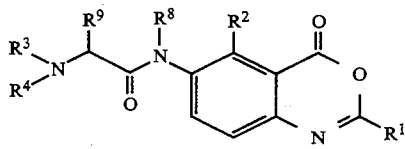
(V)

wherein R¹ and R² are lower alkyl.

12. The compound of claim 1, having the structural formula

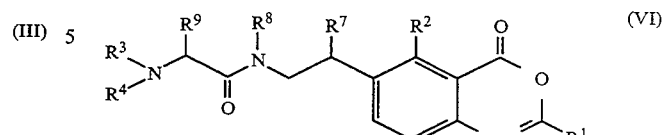
(VI)

wherein R¹ and R² are lower alkyl.

13. The compound of claim 1, having the structural formula

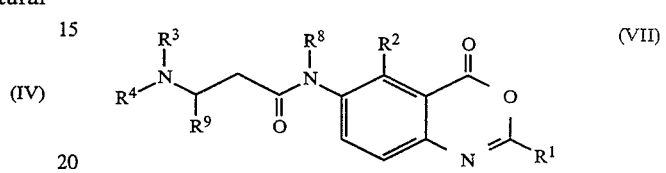
(VII)

wherein R¹ and R² are lower alkyl.

14. A pharmaceutical composition for treating disease states or physiological conditions associated with elevated HLE levels, comprising, in combination with a pharmaceutically acceptable carrier, an effective HLE modulating amount of the compound of claim 1.

15. A method for inhibiting serine proteases in an animal, comprising administering to the animal an effective serine protease inhibiting amount of the compound of claim 1.

16. A method for treating an individual having a disease or physiological condition associated with elevated HLE levels, comprising administering to such individual an effective HLE modulating amount of the compound of claim 1.

* * * * *